US008956876B2

(12) United States Patent
Sasaki et al.

(10) Patent No.: US 8,956,876 B2
(45) Date of Patent: Feb. 17, 2015

(54) METHOD FOR QUANTITATIVELY DETECTING 8-OXO 2'-DEOXYGUANOSINE IN AQUEOUS SAMPLE SOLUTION WITH HIGH SENSITIVITY

(75) Inventors: Shigeki Sasaki, Fukuoka (JP); Osamu Nakagawa, Fukuoka (JP); Zhichun Li, Fukuoka (JP); Atsushi Takaki, Fukuoka (JP); Sachiyo Saitoh, Fukuoka (JP)

(73) Assignee: TAS Project Co. Ltd, Fukuoka (JP)

( * ) Notice: Subject to any disclaimer, the term of this patent is extended or adjusted under 35 U.S.C. 154(b) by 0 days.

(21) Appl. No.: 14/007,553

(22) PCT Filed: Mar. 26, 2012

(86) PCT No.: PCT/JP2012/057750
§ 371 (c)(1),
(2), (4) Date: Oct. 28, 2013

(87) PCT Pub. No.: WO2012/133306
PCT Pub. Date: Oct. 4, 2012

(65) Prior Publication Data
US 2014/0057357 A1    Feb. 27, 2014

(30) Foreign Application Priority Data
Mar. 25, 2011    (JP) .................................. 2011-068146

(51) Int. Cl.
*G01N 33/58*    (2006.01)
*G01N 21/76*    (2006.01)
(Continued)

(52) U.S. Cl.
CPC ............ *G01N 33/582* (2013.01); *G01N 33/533* (2013.01); *G01N 33/542* (2013.01); *G01N 33/54313* (2013.01); *G01N 2021/7786* (2013.01)
USPC ................. 436/94; 436/96; 436/98; 436/164; 436/166; 436/172; 422/82.08; 422/527

(58) Field of Classification Search
USPC ............ 436/63, 86, 89, 94, 96, 98, 106, 111, 436/127, 128, 131, 164, 166, 172; 422/82.05, 82.08, 527
See application file for complete search history.

(56) References Cited

U.S. PATENT DOCUMENTS

2002/0123155 A1*  9/2002  Himmelhaus et al. ........ 436/178
2007/0077546 A1*  4/2007  Ji et al. .............................. 435/2
(Continued)

FOREIGN PATENT DOCUMENTS

EP    2 095 857 A1    9/2009
JP    A-06-065260    3/1994
(Continued)

OTHER PUBLICATIONS

Hofer et al., "A Method to Determine RNA and DNA Oxidation Simultaneously by HPLC-ECD: Greater RNA Than DNA Oxidation in Rat Liver After Doxorubicin Administration," *Biol. Chem.*, Jan. 2006, vol. 387, pp. 103-111.
(Continued)

Primary Examiner — Maureen Wallenhorst
(74) Attorney, Agent, or Firm — Oliff PLC

(57) ABSTRACT

There is provided a method for quantitatively detecting 8-oxo 2'-deoxyguanosine in an aqueous sample solution with high sensitivity. A method for quantitatively detecting 8-oxo 2'-deoxyguanosine in an aqueous sample solution, including the steps of 1) immobilizing a fluorescent probe molecule showing a fluorescence response specific to 8-oxo 2'-deoxyguanosine on surfaces of fine particles via a spacer unit and bringing the sample solution into contact with the fine particles, and 2) measuring a physical property of the fine particles before and after the contact with the sample solution to determine a change in the physical property.

7 Claims, 6 Drawing Sheets

(51) Int. Cl.
*G01N 33/533* (2006.01)
*G01N 33/542* (2006.01)
*G01N 33/543* (2006.01)
*G01N 21/77* (2006.01)

(56) References Cited

U.S. PATENT DOCUMENTS

2008/0038830 A1* 2/2008 Ure et al. .................. 436/73
2010/0035365 A1* 2/2010 Wiesner et al. ............ 436/501
2011/0159228 A1* 6/2011 Swaminathan et al. ........ 428/68

FOREIGN PATENT DOCUMENTS

JP  A-2002-253232  9/2002
JP  A-2004-354164  12/2004
WO  WO 2007/074722 A1  7/2007

OTHER PUBLICATIONS

Dizdaroglu et al., "Free Radical-Induced Damage to DNA: Mechanisms and Measurement," *Free Radical Biology & Medicine*, 2002, vol. 32, No. 11, pp. 1102-1115.

Nakae et al., "A New Technique for the Quantitative Assessment of 8-Oxoguanine in Nuclear DNA as a Marker of Oxidative Stress. Application to Dystrophin-Deficient DMD Skeletal Muscles," *Histochem. Cell Biol.*, Aug. 2005, vol. 124, pp. 335-345.

Nakagawa et al., "Specific Fluorescent Probe for 8-Oxoguanosine," *Angew. Chem. Int. Ed.*, 2007, vol. 46, pp. 4500-4503.

Nasr et al., "Selective Fluorescence Quenching of the 8-oxoG-Clamp by 8-Oxodeoxyguanosine in ODN," *Bioorganic & Medicinal Chemistry Letters*, 2009, vol. 19, pp. 727-730.

Li et al., "Synthesis of New Derivatives of 8-oxoG-Clamp for Better Understanding the Recognition Mode and Improvement of Selective Affinity," *Bioorganic & Medicinal Chemistry*, 2010, vol. 18, pp. 3992-3998.

May 22, 2012 International Search Report issued in International Application No. PCT/JP2012/057750.

Glad et al., "High-Performance Liquid Affinity Chromatography of Nucleosides, Nucleotides and Carbohyrdrates with Boronic Acid-Substituted Microparticulate Silica," Journal of Chromatography, vol. 200, pp. 254-260, 1980.

Sep. 12, 2014 Supplementary European Search Report issued in European Application No. 12764303.9.

* cited by examiner

METHOD FOR QUANTITATIVELY DETECTING 8-OXO 2'-DEOXYGUANOSINE IN AQUEOUS SAMPLE SOLUTION WITH HIGH SENSITIVITY

TECHNICAL FIELD

The present invention relates to a method for quantitatively detecting 8-oxo 2'-deoxyguanosine in an aqueous sample solution with high sensitivity, more specifically to a method for quantitatively detecting 8-oxo 2'-deoxyguanosine in an aqueous sample solution, comprising the steps of:
1) immobilizing a fluorescent probe molecule showing a fluorescence response specific to 8-oxo 2'-deoxyguanosine on the surfaces of fine particles via a spacer unit and bringing the sample solution into contact with the fine particles; and
2) measuring a physical property of the fine particles before and after the contact with the sample solution to determine the change in the physical property.

BACKGROUND ART 8-oxo 2'-deoxyguanosine (hereinafter also called 8-oxo-dG) is attracting attention as an oxidative stress marker because it directly reflects the quantity of reactive oxygen generated by environmental factors or associated with metabolic activities in a living body. Thus, accurate measurement of the quantity of 8-oxo-dG present in a living body or in urine is extremely significant for studies of mutation, aging, and many diseases. Several methods for detecting 8-oxo-dG have been developed, including instrumental analysis such as the HPLC-ECD method, which combines HPLC and an electrochemical detector (see, for example, Non-Patent Document 1) and the GC-MS method, which uses gas chromatography and a mass spectrometer (see, for example, Non-Patent Document 2), and the ELISA method with monoclonal antibodies (see, for example, Non-Patent Document 3).

With these detection methods, however, it is difficult to quantitatively observe the presence of 8-oxo-dG in real time in a living cell.

To overcome the problem, a low-molecular-weight fluorescent probe showing a fluorescence response specific to 8-oxo-dG has been developed (see, for example, Non-Patent Documents 4 and 5).

The low-molecular-weight fluorescent probe recognizes 8-oxo-dG through formation of multiple hydrogen bonds with 8-oxo-dG in an organic solvent and shows specific fluorescence quenching. Thus, the quantity of 8-oxo-dG present in the system can be detected by measuring the degree of fluorescence quenching.

Among a variety of derivatives of the low-molecular-weight fluorescent probe, a low-molecular-weight fluorescent probe showing a fluorescence response specific to 2'-deoxyguanosine (hereinafter also called dG) has been found (see, for example, Non-Patent Document 6).

Shown below are a mode (A) in which the low-molecular-weight fluorescent probe showing a fluorescence response specific to 8-oxo-dG recognizes 8-oxo-dG and forms multiple hydrogen bonds and a mode (B) in which the low-molecular-weight fluorescent probe showing a fluorescence response specific to dG recognizes dG and foams multiple hydrogen bonds.

It is reported that the low-molecular-weight fluorescent probe showing a fluorescence response specific to 8-oxo-dG shown in A has a complexation ability with 8-oxo-dG in a chloroform solution that is 10 times that with dG, and the low-molecular-weight fluorescent probe showing a fluorescence response specific to dG shown in B has a complexation ability with dG in a chloroform solution that is 25 times that with 8-oxo-dG.

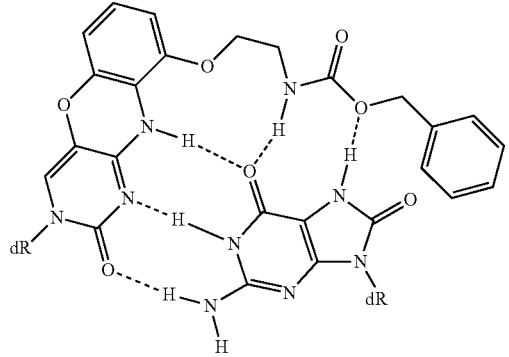

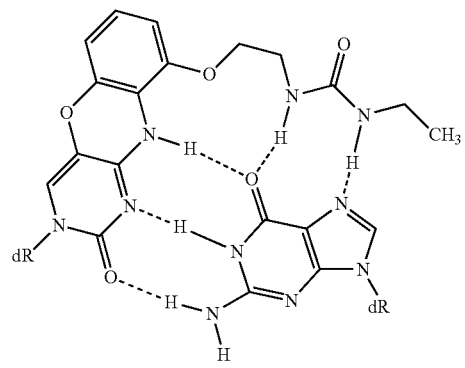

The low-molecular-weight fluorescent probe showing a fluorescence response specific to 8-oxo-dG precisely recognizes 8-oxo-dG through multiple hydrogen bonds, and hydrogen bonds hardly act in water that is a protic polar solvent. Thus, the fluorescent probe cannot recognize 8-oxo-dG through multiple hydrogen bonds in water, so it was difficult to directly detect highly water-soluble 8-oxo-dG in an aqueous solution such as urine.

In addition, the usual concentration of 8-oxo-dG in urine is reported to be extremely low of 10 ng/mL to 20 ng/mL (corresponding to 35 nM to 70 nM assuming a molecular weight to be 283). Therefore, the low-molecular-weight fluorescent probe needs to be improved for higher sensitivity to enable detection of 8-oxo-dG at lower concentrations, in order to use the probe for detection of 8-oxo-dG in urine.

PRIOR ART DOCUMENTS

Non-Patent Documents

Non-Patent Document 1: Hofer, T., Sea, A. Y., Prudencio, M., Leeuwenburgh, C.; Biol. Chem., 387, p. 103-113 (2006)
Non-Patent Document 2: Dizdaroglu, M., Jaruga, P., Birincioglu, M., Rodriguez, H.; Free Radical Biol. Med., 32, p. 1102-1105 (2002)
Non-Patent Document 3: Nakae, Y., Stoward, P. J., Bespalov, I. A., Melamede, Wallace, S. S.; Histochem. Cell Biol., 124, p. 335-345 (2005)
Non-Patent Document 4: Nakagawa, O., Ono, S., Li, Z., Tsujimoto, A., Sasaki, S.; Angew. Chem. Int. Ed., 46, p. 4500-4503 (2007)

Non-Patent Document 5: Nasr, T., Li, Z., Nakagaw, O., Taniguchi, Y., Sasaki, S.; Bioorg. Med. Chem. Lett., 19, p. 727-730 (2009)

Non-Patent Document 6: Li, Z., Nakagawa, O., Koga, Y., Taniguchi, Y., Sasaki, S.; Bioorg. Med. Chem., 18, p. 3992-3998 (2010)

SUMMARY OF THE INVENTION

Problem to be Solved by the Invention

An object of the present invention is to provide a method for quantitatively detecting 8-oxo 2'-deoxyguanosine (8-oxo-dG) in an aqueous sample solution with high sensitivity.

Means for Solving the Problem

As a result of intensive study to solve the problem, the inventors of the present invention, etc. have found the following. That is, immobilization of a fluorescent probe molecule showing a fluorescence response specific to 8-oxo-dG on the surfaces of fine particles via a spacer unit font's minute hydrophobic space on the surfaces of the fine particles, which allows the probe molecule to recognize 8-oxo-dG through formation of multiple hydrogen bonds even if an aqueous sample solution is used. As a result, it is possible to quantitatively detect 8-oxo-dG and significantly improve detection sensitivity to the degree sufficient for, for example, quantitative detection of 8-oxo-dG in urine. Thus, the inventors have completed the invention.

In addition, it is also possible to provide a device for use for quantitative detection of 8-oxo-dG with high sensitivity.

Specifically, the present invention relates to:

[1] a method for quantitatively detecting 8-oxo 2'-deoxyguanosine in an aqueous sample solution, comprising the steps of:

1) immobilizing a fluorescent probe molecule showing a fluorescence response specific to 8-oxo 2'-deoxyguanosine on the surfaces of fine particles via a spacer unit and bringing the sample solution into contact with the fine particles; and 2) measuring a physical property of the fine particles before and after the contact with the sample solution to determine the change in the physical property;

[2] the method according to [1], in which the fluorescent probe molecule showing a fluorescence response specific to 8-oxo 2'-deoxyguanosine is a molecule of Formula (1)

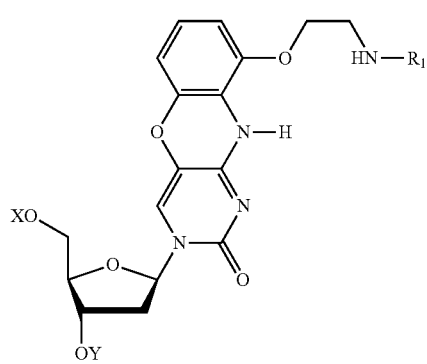

(1)

(where $R_1$ is a 6-amino-2-pyridyl group or $—CO_2(CH_2)_1R_2$ (where $R_2$ is a hydrogen atom or a $C_{6-16}$ aryl group, and l is an integer of 1 to 3); and one of X and Y is a protecting group of the hydroxyl group and the other is the spacer unit);

[3] the method according to [2], in which X is the spacer unit (where the spacer unit is $—(CH_2)_m—NHCO—$ (where m is an integer of 2 to 10)), and Y is $—SiR_3R_4R_5$ (where $R_3$, $R_4$, and $R_5$ are each independently a methyl group, a tert-butyl group, or a phenyl group);

[4] the method according to any one of [1] to [3], in which the fine particles are inorganic particles or polymer resin particles, and the change in the physical property is determined by measurement of the fluorescence intensity;

[5] the method according to [4], in which the inorganic particles are silica gel particles;

[6] the method according to [4] or [5], in which the quantitative detection is carried out by drying the fine particles in a microplate well to adhere to the well, adding the aqueous sample solution to the well, and measuring the fluorescence intensity of the fine particles with heating;

[7] the method according to [4] or [5], in which the quantitative detection is carried out by packing a column with the fine particles, passing the aqueous sample solution through the column, and measuring the fluorescence intensity of the fine particles thus packed;

[8] a silica gel particle having a molecule of Formula (1) immobilized on the surface via a spacer unit:

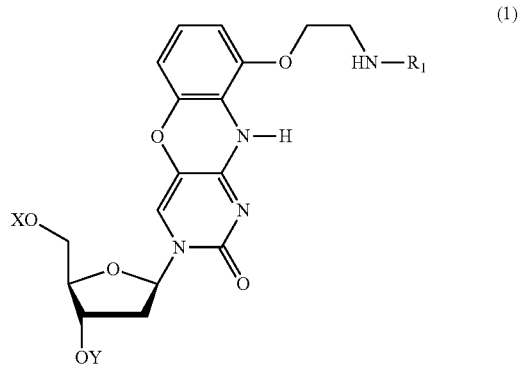

(1)

(where $R_1$ is a 6-amino-2-pyridyl group or $—CO_2(CH_2)_1R_2$ (where $R_2$ is a hydrogen atom or a $C_{6-46}$ aryl group, and l is an integer of 1 to 3); and one of X and Y is a protecting group of the hydroxyl group and the other is the spacer unit);

[9] the silica gel particle according to [8], in which X is the spacer unit (where the spacer unit is $—(CH_2)_m—NHCO—$ (where m is an integer of 2 to 10)), and Y is $—SiR_3R_4R_5$ (where $R_3$, $R_4$, and $R_5$ are each independently a methyl group, a tert-butyl group, or a phenyl group); and

[10] a separation column for separating 8-oxo 2'-deoxyguanosine, comprising the silica gel particle as described in [8] or [9] as a packing material.

Effects of the Invention

According to the present invention, a method for quantitatively detecting 8-oxo-dG in an aqueous sample solution with high sensitivity can be provided.

The method according to the present invention can achieve highly sensitive quantitative detection of 8-oxo-dG with easy operation through the use of a fluorescent probe molecule showing a fluorescence response specific to 8-oxo-dG, so the method can be considered to be an excellent method.

FIG. 1 shows a schematic diagram of the present invention.

As shown in FIG. 1, immobilization of a fluorescent probe molecule 2 showing a fluorescence response specific to 8-oxo-dG on the surfaces of fine particles 1 via a spacer unit 3 forms minute hydrophobic space 6 on the surfaces, which allows only 8-oxo-dG 4, among dG 5 and 8-oxo-dG 4 present in aqueous phase 7, to form multiple hydrogen bonds with the probe molecule 2 in the minute hydrophobic space 6, resulting in fluorescence quenching of only the probe molecule 2 having multiple hydrogen bonds with 8-oxo-dG 4.

MODES FOR CARRYING OUT THE INVENTION

Figure 1:
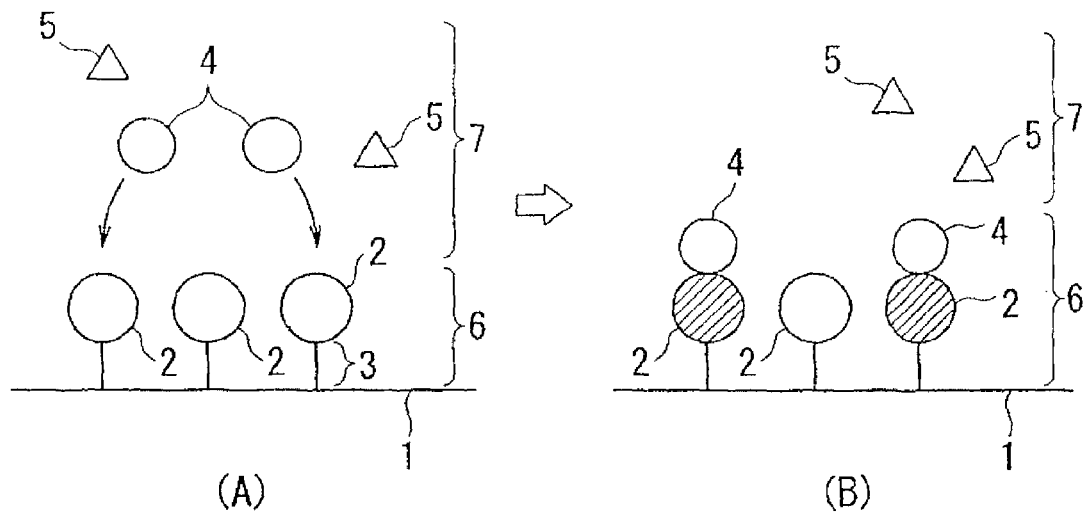
FIGS. 1(a) and 1(b) are schematic diagrams illustrating the present invention.

The present invention will be described in more detail.

The method of the present invention for quantitatively detecting 8-oxo 2'-deoxyguanosine in an aqueous sample solution comprises the steps of:
1) immobilizing a fluorescent probe molecule showing a fluorescence response specific to 8-oxo 2'-deoxyguanosine via a spacer unit on the surfaces of fine particles and bringing the sample solution into contact with the fine particles; and
2) measuring a physical property of the fine particles before and after the contact with the sample solution to determine the change in the physical property.

The aqueous sample solutions that may be used in the present invention are not particularly limited, provided that the solutions contain any 8-oxo-dG. Examples include aqueous solutions derived from biological cells taken from animals including human, plants, bacteria, and fungi (for example, blood, urine, other body fluids, tissue lysates, and cell lysates). Aqueous solutions present inside living bodies such as intracellular fluid and extracellular fluid are also included in the concept of the aqueous sample solution of the present invention.

Further aqueous sample solutions which may be used in the present invention include aqueous solutions such as food containing natural and artificial chemical substances, cosmetics, pharmaceuticals, and aqueous solutions of, for example, recycled products using wastes as raw materials, and water extracted from soil and atmospheric components, and environmental water.

The method of quantitative detection that may be used in the present invention may be achieved through fluorescence measurement and may also be achieved through measurement of absorption spectra, in particular ultraviolet absorption spectra.

The quantitative detection through fluorescence measurement is achieved by irradiating a sample with an ultraviolet ray having a wavelength of 300 nm to 400 nm, preferably 330 nm to 380 nm, and more preferably 345 nm to 365 nm as an excitation ray and measuring the intensity of an emitted fluorescence having a wavelength of 410 nm to 520 nm and preferably 420 nm to 470 nm.

A specific method of quantitative detection through fluorescence quenching is achieved by adding 8-oxo-dG in various standard concentrations to the fine particles, to which a fluorescent probe molecule has been immobilized, measuring the fluorescence intensities to make a calibration curve, and comparing the fluorescence intensity measured with a sample solution with the calibration curve to calculate the concentration of 8-oxo-dG.

A specific method of quantitative detection through absorption spectra is achieved by adding 8-oxo-dG in various concentrations to the fine particles, to which a fluorescent probe molecule has been immobilized, measuring absorption spectra of ultraviolet ray etc. to make a calibration curve based on the quantities of changes in the wavelength range in which absorption spectra change most significantly, and comparing the quantity of changes in that wavelength range in the absorption spectrum measured with a sample solution with the calibration curve to calculate the concentration of 8-oxo-dG.

Fine particles that may be used in the present invention may be inorganic particles or polymer resin particles and the average particle diameter ranges, for example, from 0.001 μm to 100 μm, and preferably from 0.1 μm to 50 μm or from 1 μm to 20 μm.

Examples of inorganic particles include silicon particles (silica gel particles), quartz glass particles, alumina particles, graphite particles, carbon nanotube particles, graphene particles, and fullerene particles.

Examples of polymer resin particles include particles made from poly-N-dodecylacrylamide (PDDA), poly(phenylacetylene), poly(phenylene butadiynylene), polypyrrole, polymethyl methacrylate (PMMA), polyvinyl alcohol, polystyrene, and cellulose.

Examples of the fluorescent probe molecule that is immobilized on the surfaces of the fine particles via a spacer unit and that shows a fluorescence response specific to 8-oxo-dG include a molecule of Formula (1):

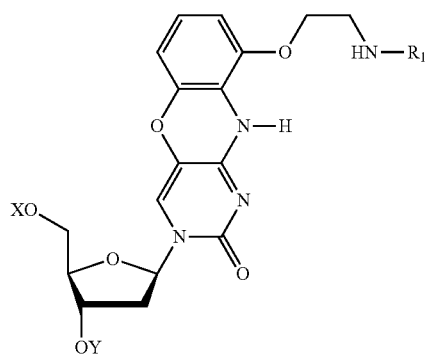

(where $R_1$ is a 6-amino-2-pyridyl group or —$CO_2(CH_2)_l R_2$ (where $R_2$ is a hydrogen atom or a $C_{6-16}$ aryl group and l is an integer of 1 to 3); and one of X and Y is a protecting group of the hydroxyl group and the other is a spacer unit).

Examples of the $C_{6-16}$ aryl group include a phenyl group, a naphthyl group, a biphenyl group, an anthracenyl group, a phenanthrenyl group, and a pyrenyl group.

Examples of the protecting group of the hydroxy group include a trimethylsilyl group, a tert-butyldimethylsilyl group, a tert-butyldiethylsilyl group, a tert-butyldiphenylsilyl group, a methoxymethyl group, an ethoxymethyl group, an ethoxyethyl group, a methoxyethoxymethyl group, a tert-butoxycarbonyl group, and a benzyloxycarbonyl group.

The spacer unit is not particularly limited, provided that the spacer unit is used in the field of organic chemistry. Specific examples of the spacer unit include —$(CH_2CH_2O)_j$—$CH_2CH_2$—, —$(CH_2CH_2O)_3$—$CH_2CH_2CO$—, —$(CH_2CH_2O)_j$—$CCH_2CH_2SCO$—, —$(CH_2CH_2O)_j$—$CH_2CH_2NHCO$—, —$(CH_2CH_2O)_j$—$CO$—, —$(CH_2CH_2O)_j$—$CS$—, —$(CH_2)_k$—, —$(CH_2)_k$—$CO$—, —$(CH_2)_k$—$OCO$—, —$(CH_2)_k$—$SCO$—, and —$(CH_2)_k$—$NHCO$—.

In the above formulae, j is an integer of 1 to 10 and preferably an integer of 1 to 4; and k is an integer of 2 to 30 and preferably an integer of 2 to 12.

The spacer unit may be immobilized on the surfaces of the fine particles through physical adsorption or covalent bond of carbon atoms, sulfur atoms, oxygen atoms, or nitrogen atoms.

A preferred fluorescent probe molecule showing a fluorescence response specific to 8-oxo-dG is a molecule in which X is a spacer unit (where the spacer unit is —$(CH_2)_m$—NHCO— (where m is an integer of 2 to 10)), and Y is —$SiR_3R_4R_5$ (where $R_3$, $R_4$, and $R_5$ are each independently a methyl group, a tert-butyl group, or a phenyl group).

The molecule with m of 3 is more preferred.

A preferred method of quantitatively detecting 8-oxo-dG in an aqueous sample solution is the method in which the fine particles are inorganic particles or polymer resin particles and the quantitative detection is carried out based on the degree of fluorescence quenching or based on the degree of fluorescence quenching and the degree of the change in absorption spectra.

Specific examples of the inorganic particles and polymer resin particles and the particles diameter as well as method of the quantitative detection based on the degree of fluorescence quenching or based on the degree of fluorescence quenching and the degree of the change in absorption spectra are as described above.

The method in which the fine particles are inorganic particles and the inorganic particles are silica gel particles is preferred.

As a preferred embodiment of the present invention, the method may be mentioned in which the quantitative detection is carried out by placing the fine particles in a microplate well, drying the particles to adhere to the well, adding the aqueous sample solution to the well, and measuring the fluorescence intensity of the fine particles with heating.

The microplate used is not particularly limited and a commercially available 96-well or 384-well microplate may be used.

This embodiment involves placing in a well, for example, an aqueous suspension of fine particles having a (8-oxo-dG selective) fluorescent probe molecule immobilized on the surfaces, heating to evaporate water and allow the fine particles to adhere to the surface of the well, and adding an aqueous sample solution and heating.

The quantity of the fine particles used is 10 ng to 500 ng and preferably 20 ng to 400 ng, or 40 ng to 200 ng per well. The aqueous suspension is obtained by suspending, for example, 1 ng to 100 ng and preferably 5 ng to 60 ng of the fine particles in 1 μL. The heating temperature for evaporating water is 40° C. to 60° C., preferably 45° C. to 55° C., and for example, 50° C., and the heating time is 30 minutes to 4 hours, preferably 1 hour to 3 hours, and for example, 2 hours.

The quantity of the aqueous sample solution used is 24 to 10 μL and preferably 2 μL to 4 μL per well, and the heating temperature is 40° C. to 60° C., preferably 45° C. to 55° C., and for example, 50° C., and the heating time is 30 minutes to 4 hours, preferably 1 hour to 2 hours, and for example, 1 hour.

The fluorescence intensity of the fine particles is measured with heating by using, for example, a microplate reader or other means, which provides the degree of fluorescence quenching of the fine particles and, hence the quantity of 8-oxo-dG that has accumulated on the fine particles can be obtained. This allows calculation of the initial concentration of 8-oxo-dG in the sample solution. Thus, the method is advantageous for quantification of a sample solution containing a very small quantity of 8-oxo-dG.

As another preferred embodiment of the present invention, the method may be mentioned in which the fine particles are packed in a column and the aqueous sample solution is allowed to pass through the column and the quantitative detection of 8-oxo-dG is carried out based on the degree of fluorescence quenching of the packed fine particles or based on the degree of fluorescence quenching and the degree of the change in absorption spectra.

Figure 2:
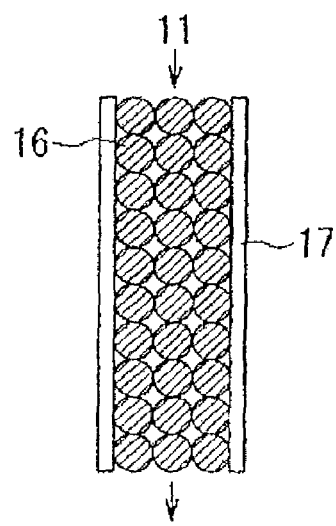
FIG. 2 is a schematic diagram illustrating an embodiment in which a column packed with the fine particles with a (8-oxo-dG selective) fluorescent probe molecule is used.

FIG. 2 shows a schematic diagram of this embodiment of the present invention.

As shown in FIG. 2, the fine particles 16 having a (8-oxo-dG selective) fluorescent probe molecule immobilized thereon is packed in a column 17 and, after passing the sample solution 11 through the column 17, quantitative detection of 8-oxo-dG in the sample solution is carried out based on the degree of fluorescence quenching of the packed fine particles 16.

This embodiment is advantageous when the sample solution contains a very small quantity of 8-oxo-dG. This is because after a certain quantity of the sample solution is passed to accumulate 8-oxo-dG on the fine particles 16, the degree of fluorescence quenching of the fine particles 16 can be measured to provide the quantity of 8-oxo-dG that has accumulated on the fine particles 16, which enables calculation of the initial concentration of 8-oxo-dG in the sample solution.

The column containing the fine particles 16 having a (8-oxo-dG selective) fluorescent probe molecule immobilized thereon as a packing material as shown in FIG. 2 can be used as a separation column for separating 8-oxo-dG by using an eluent capable of eluting 8-oxo-dG.

The present invention also relates to silica gel particles having a molecule of Formula (1):

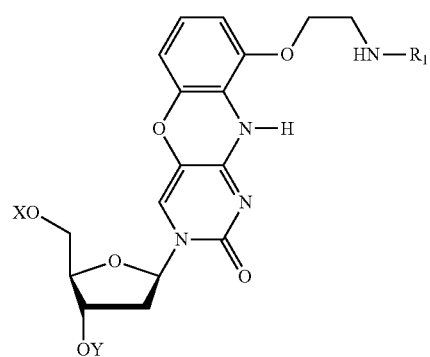

(where $R_1$ is a 6-amino-2-pyridyl group or $-CO_2(CH_2)_l R_2$ (where $R_2$ is a hydrogen atom or a $C_{6-16}$ aryl group and l is an integer of 1 to 3); and one of X and Y is a protecting group of the hydroxyl group and the other is a spacer unit) immobilized on the surfaces via a spacer unit.

The average particle diameter of the silica gel particles used ranges, for example, from 0.001 μm to 100 μm, and preferably from 0.1 μm to 10 μm (for high sensitivity measurement) or from 10 μm to 100 μm (for separation column).

Examples of the $C_{6-16}$ aryl group include a phenyl group, a naphthyl group, a biphenylyl group, an anthracenyl group, a phenanthrenyl group, and a pyrenyl group.

Examples of the protecting group of the hydroxy group include a trimethylsilyl group, a tert-butyldimethylsilyl group, a tert-butyldiethylsilyl group, a tert-butyldiphenylsilyl group, a methoxymethyl group, an ethoxymethyl group, an ethoxyethyl group, a methoxyethoxymethyl group, a tert-butoxycarbonyl group, and a benzyloxycarbonyl group.

The spacer unit is not particularly limited, provided that the spacer unit is used in the field of organic chemistry. Specific examples of the spacer unit include $-CH_2CH_2O)_j-CH_2CH_2-$, $-(CH_2CH_2O)_j-CH_2CH_2CO-$, $-(CH_2CH_2O)_j-CCH_2CH_2SCO-$, $-(CH_2CH_2O)_j-CH_2CH_2NHCO-$, $-(CH_2CH_2O)_j-CO-$, $-(CH_2CH_2O)_j-CS-$, $-(CH_2)_k-$, $-(CH_2)_k-CO-$, $-(CH_2)_k-OCO-$, $-(CH_2)_k-SCO-$, and $-(CH_2)_k-NHCO-$.

In the above formulae, j is an integer of 1 to 10 and preferably an integer of 1 to 4; and k is an integer of 2 to 30 and preferably an integer of 2 to 12.

The spacer unit may be immobilized on the surfaces of the fine particles through physical adsorption or covalent bond of carbon atoms, sulfur atoms, oxygen atoms, or nitrogen atoms.

Preferably, the silica gel particles in which X is a spacer unit (where the spacer unit is $-(CH_2)_m-NHCO-$ (where m is an integer of 2 to 10)), and Y is $-SiR_3R_4R_5$ (where $R_3$, $R_4$, and $R_5$ are each independently a methyl group, a tert-butyl group, or a phenyl group) may be mentioned.

The method for preparing the silica gel particles having the molecule of Formula (1) immobilized thereon will now be described.

The method for preparing the silica gel particles (1-A) having a molecule of Formula (1) with the spacer unit of $-(CH_2)_m-NHCO-$ immobilized thereon is shown in Scheme 1 below (where $R_1$, Y, and m have the same meanings as above).

Scheme 1

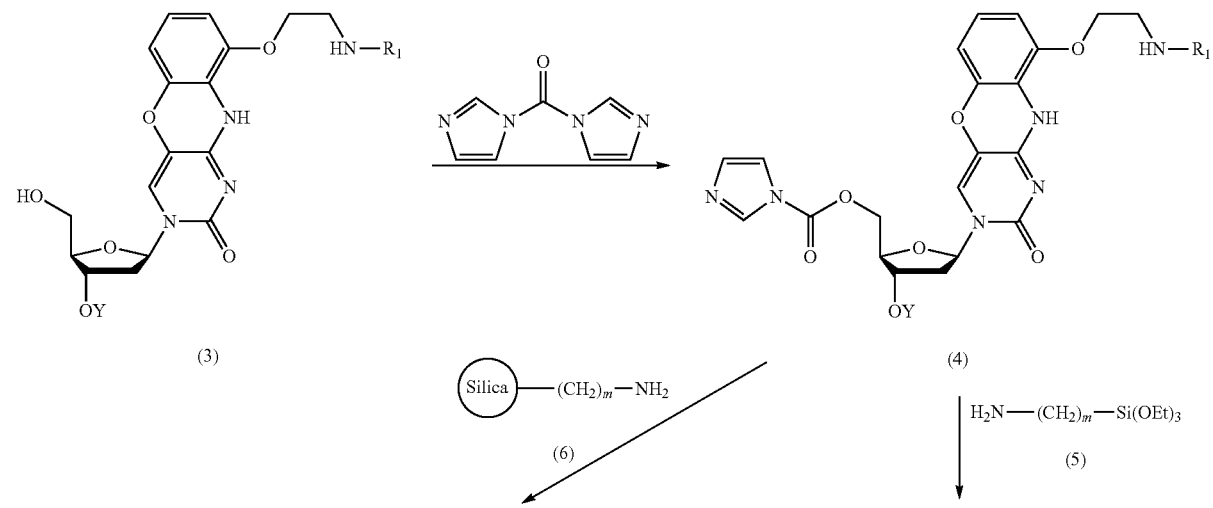

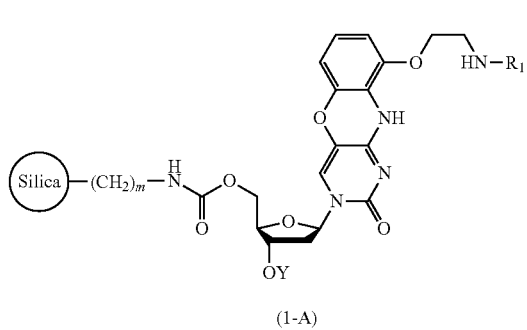

(1-A)

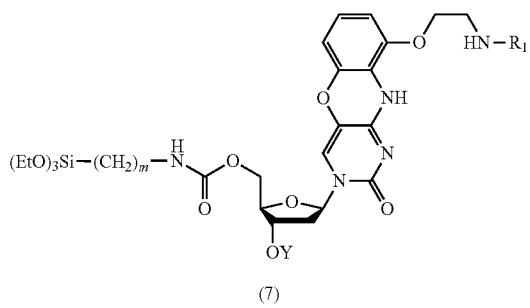

(7)

Specifically, the primary hydroxy group of the compound (3) is reacted with carbonyldiimidazole to obtain the compound (4), which is reacted with the silica gel particles (6) modified with an alkylamino group, or reacted with the reagent of Formula (5) followed by reaction with silica gel particles, to obtain the silica gel particles (1-A).

By using the method, other inorganic particles or polymer resin particles having a molecule of Formula (1) immobilized thereon via various spacer units, for example, $-(CH_2CH_2O)_j-CH_2CH_2-$, $-(CH_2CH_2O)_j-CH_2CH_2CO-$, $-(CH_2CH_2O)_k-CCH_2CH_2SCO-$, $-(CH_2CH_2O)_j-CH_2CH_2NHCO-$, $-(CH_2CH_2O)_j-CO-$, $-(CH_2CH_2O)_j-CS-$, $-(CH_2)_k-$, $-(CH_2)_k-CO-$, $-(CH_2)_k-OCO-$, $-(CH_2)_k-SCO-$, and $-(CH_2)_k-NHCO-$ (where j and k have the same meanings as above) through physical adsorption or covalent bond of carbon atoms, sulfur atoms, oxygen atoms, or nitrogen atoms can be prepared.

The method for preparing the compound (3-A) having $R_1$ of $-CO_2(CH_2)_lR_2$, among the compound (3) of Scheme 1, is shown in Scheme 2 (where $R_2$ and l have the same meanings as above; $Y_2$ is a protecting group different from Y, for example, a 4,4'-dimethoxytrityl group; and $X_2$ is a leaving group, for example, a halogen atom such as a chlorine or bromine atom or a sulfonyl group such as methanesulfonyl or p-toluenesulfonyl).

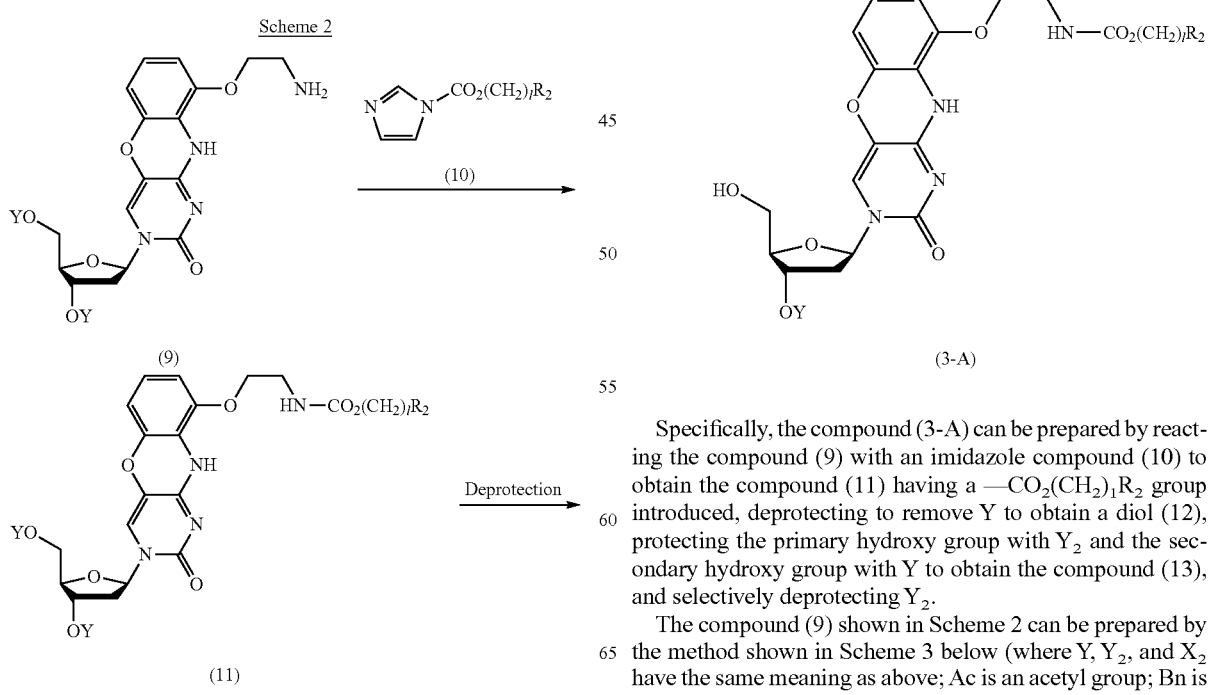

Specifically, the compound (3-A) can be prepared by reacting the compound (9) with an imidazole compound (10) to obtain the compound (11) having a $-CO_2(CH_2)_lR_2$ group introduced, deprotecting to remove Y to obtain a diol (12), protecting the primary hydroxy group with $Y_2$ and the secondary hydroxy group with Y to obtain the compound (13), and selectively deprotecting $Y_2$.

The compound (9) shown in Scheme 2 can be prepared by the method shown in Scheme 3 below (where Y, $Y_2$, and $X_2$ have the same meaning as above; Ac is an acetyl group; Bn is a benzyl group; and DIAD is diisopropyl azodicarboxylate).

Scheme 3

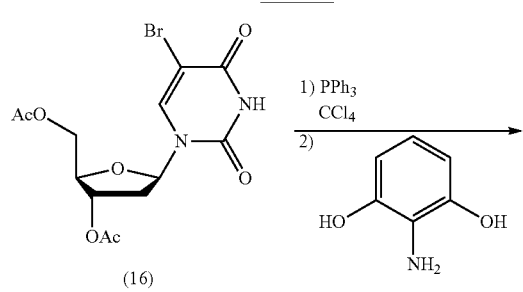
(16)

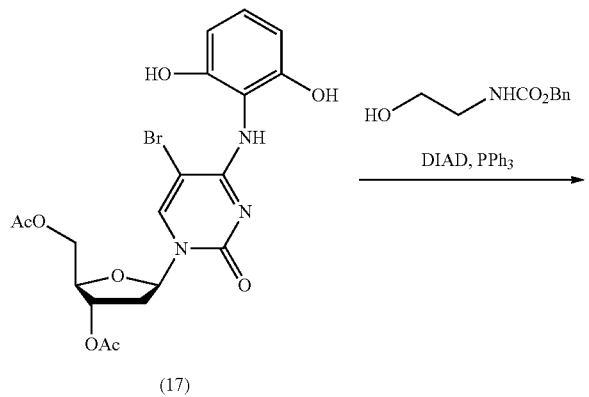
(17)

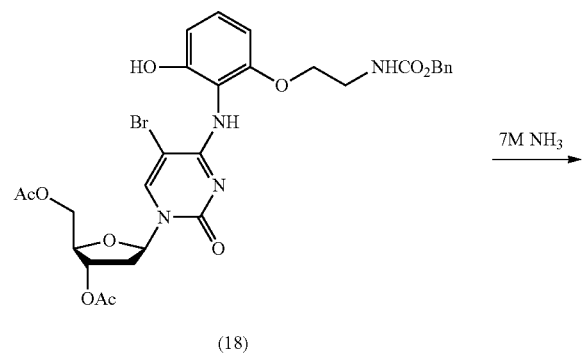
(18)

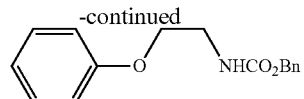

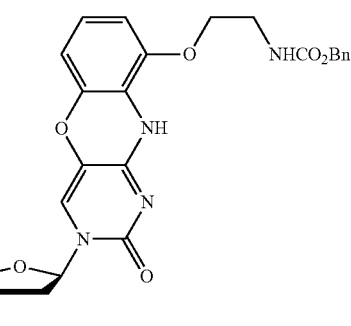
(19)

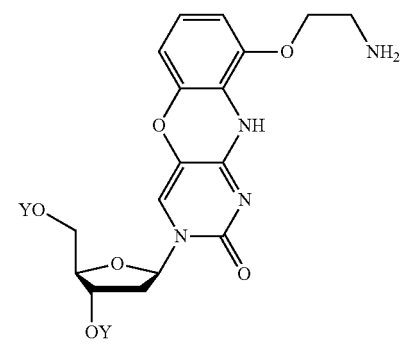
(20)

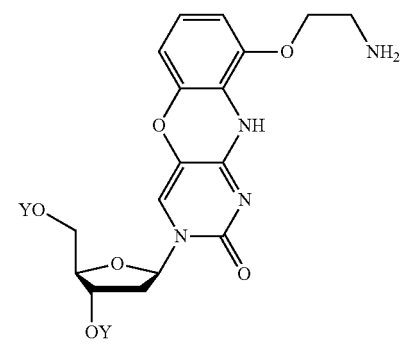

(9).

Specifically, the compound (9) can be prepared by reacting diacetate of 5-bromo-2'-deoxyuridine (16) with 2-aminoresorcinol to obtain the compound (17), reacting the compound (17) with benzyl (2-hydroxyethyl)carbamate to obtain the compound (18), reacting the compound (18) with ammonia to effect cyclization and deacetylation to obtain the compound (19), reacting the compound (19) with $YX_2$ to obtain the compound (20) having Y introduced, and removing $CO_2Bn$ from the compound (20) under hydrogenolysis conditions.

The method for preparing the compound (3-B) having $R_1$ of 6-amino-2-pyridyl group, among the compound (3) of Scheme 1, is shown in Scheme 4 (where Y, Ac, and DIAD have the same meaning as above).

Scheme 4
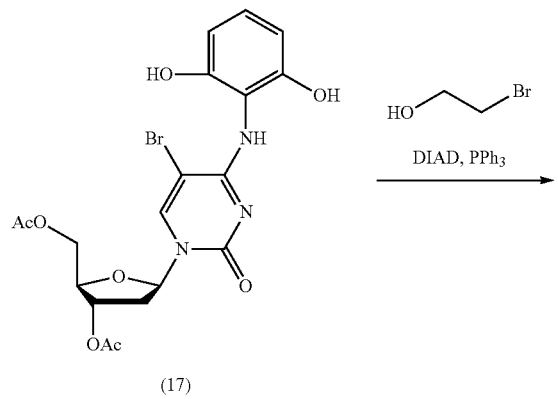
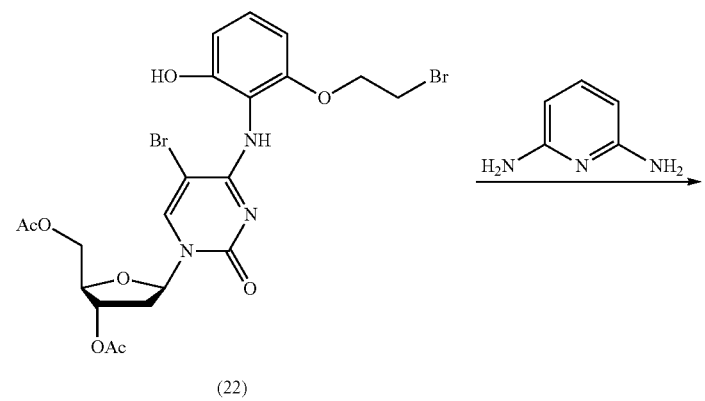
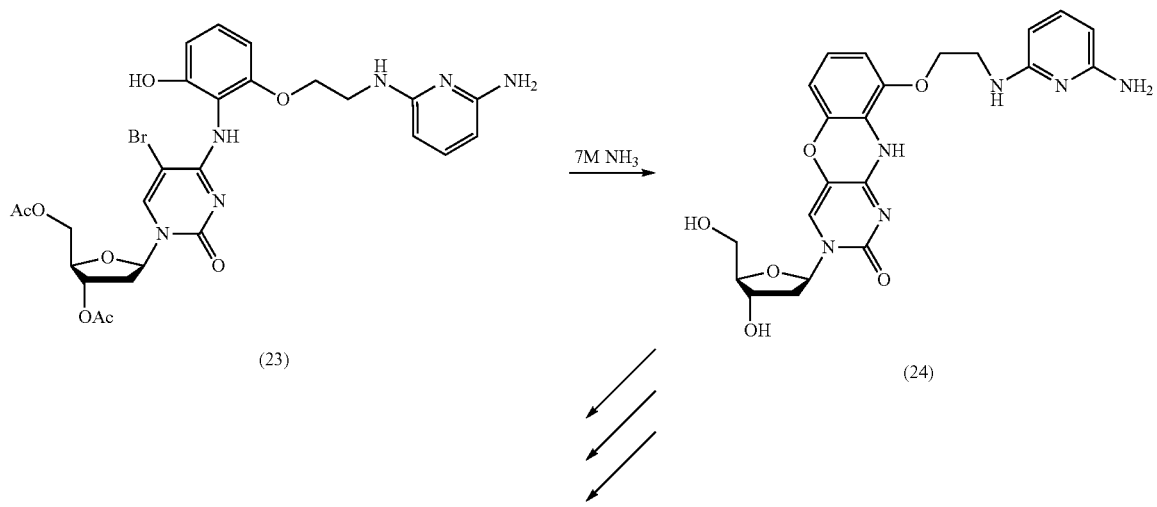

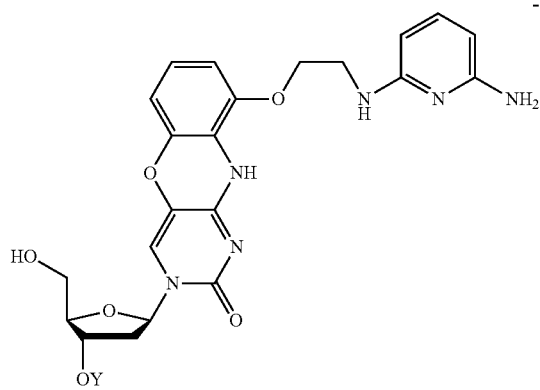

(3-B)

Specifically, the compound (17) of Scheme 3 as a starting material is reacted with 2-bromoethanol to obtain the compound (22), which is reacted with 2,6-diaminopyridine to obtain the compound (23). The compound (23) is reacted with ammonia to effect cyclization and deacetylation to obtain the compound (24), which is further processed according to Scheme 2 to obtain the compound (3-B) having only the secondary hydroxy group protected with Y.

The compound (3-A) shown in Scheme 2 can also be prepared from the compound (19) shown in Scheme 3 according to Scheme 5 below (where Y, $R_2$, 1, and Bn have the same meanings as above).

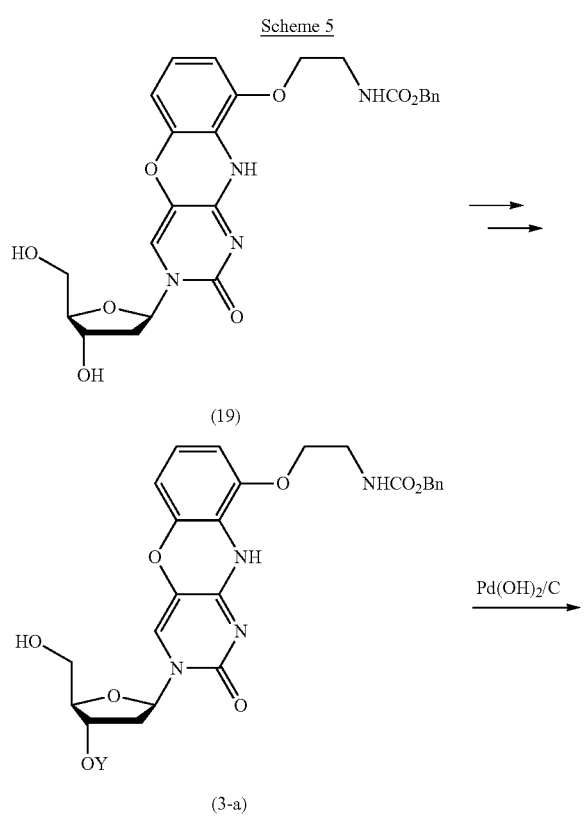

Scheme 5

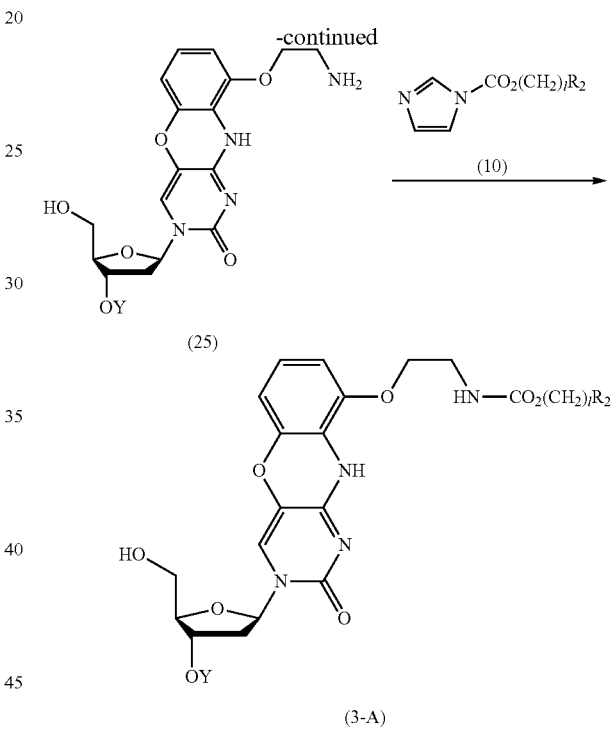

Specifically, the compound (19) is converted to the compound (3-a) according to the method illustrated in Scheme 2, and $CO_2Bn$ is removed under hydrogenolysis conditions to obtain the compound (25). The compound (25) is reacted with an imidazole compound (10) to introduce a $—CO_2(CH_2)_1R_2$ group to prepare the compound (3-A).

The silica gel particles having the molecule of Formula (1) prepared as described above have minute hydrophobic space on the surfaces of the silica gel particles because the particles have the probe molecule immobilized on the surfaces of the silica gel particles, which allows quantitative assay of 8-oxo-dG in an aqueous sample solution which would be difficult if the probe molecule was not immobilized.

In addition, by immobilizing the probe molecule on the surfaces of the silica gel particles, the sensitivity increases significantly, for example, to a level at which quantitative detection of 8-oxo-dG in urine is possible.

This allows quantitative assay of a very small quantity of 8-oxo-dG in a sample solution with high accuracy.

Therefore, the silica gel particles having the molecule of Formula (1) immobilized thereon can be a device for quantitative assay.

The silica gel particles having the molecule of Formula (1) immobilized thereon can be used as a packing material of a separation column.

The separation column containing the silica gel particles having the molecule of Formula (1) immobilized thereon can be advantageously used as a separation column for separating 8-oxo-dG by using an eluent capable of eluting 8-oxo-dG.

Specifically, because the separation column uses the silica gel particles having a selective affinity for 8-oxo-dG, only the retention time of 8-oxo-dG, among the components in the sample solution, can be changed. Therefore, even when the sample solution contains a component having the same retention time as that of 8-oxo-dG or a component having a retention time close to that of 8-oxo-dG and quantification of 8-oxo-dG is difficult, only the retention time of 8-oxo-dG can be changed so as to accurately quantify 8-oxo-dG.

EXAMPLES

Preparation Example 1

Preparation of the Compound (16)

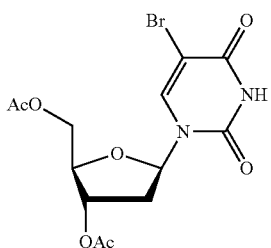

(16)

Under argon stream, 5-bromo-2'-deoxyuridine (2 g, 6.512 mmol) was dissolved in 5 mL of anhydrous pyridine and stirred. Acetic anhydride (1.54 mL, 16.28 mmol) was added dropwise to the mixture and stirred at room temperature. After 18 hours, the reaction liquid was diluted with 15 mL of ethyl acetate. The mixture was washed with a saturated sodium bicarbonate aqueous solution, water, and a saturated saline solution. The organic phase was dried over sodium sulfate and the solvent was distilled off under reduced pressure. 5 mL of toluene was added to the residue and the solvent was distilled off under reduced pressure. The resultant crude product was recrystallized from ethyl acetate/hexane to obtain 2.37 g of the compound (16) with a yield of 93%.
$^1$H-NMR (400 MHz, CDCl$_3$) δ ppm: 8.46 (1H, s), 7.87 (1H, s), 6.27 (1H, dd, J=3.6 Hz, 5.9 Hz), 5.22-5.21 (1H, m), 4.41-4.10 (3H, m), 2.56-2.50 (1H, m), 2.18-2.13 (1H, m), 2.16 (3H, s), 2.10 (3H, s).

ESI-MS (m/z): 413.02 (M+Na)$^+$

IR (cm$^{-1}$): 3013, 2824, 1744, 1710, 1687 m.p.° C.: 151.8-152.8° C.

Preparation Example 2

Preparation of the Compound (17)

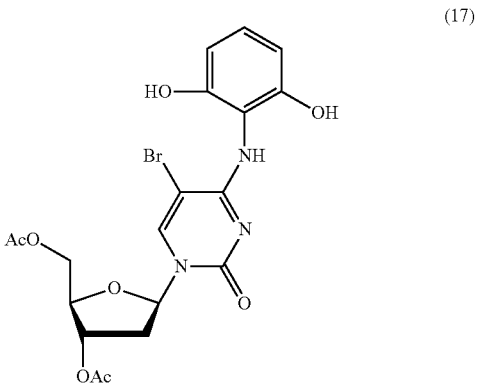 [SMILES: CC(=O)OC[C@H]1O[C@@H](n2cc(Br)c(Nc3c(O)cccc3O)nc2=O)C[C@H]1OC(C)=O]

(17)

Under argon stream, the compound (16) (3.0 g, 7.69 mmol) and triphenylphosphine (3.05 g, 11.6 mmol) were azeotroped with anhydrous acetonitrile-anhydrous dichloromethane (20 mL-5 mL) three times and with anhydrous dichloromethane once. Anhydrous carbon tetrachloride-dichloromethane (15 mL-15 mL) were added and heated to reflux. After 2.5 hours, the reaction liquid was cooled to room temperature and diazabicycloundecene (2.53 mL, 16.9 mmol), 2-aminoresorcinol (1.92 g, 15.4 mmol) were added and stirred. The solvent of the reaction liquid was distilled off under reduced pressure. Dichloromethane-hexane (16 mL-16 mL) was added to the residue and the mixture was vigorously stirred at room temperature. 85 mL of a 5% citric acid aqueous solution was added and the precipitate was suction-filtrated. The filtration residue was washed with water, dichloromethane, and acetonitrile. 3.1 g of the compound (17) was obtained with a yield of 81%.

$^1$H-NMR (400 MHz, DMSO-d$_6$) δ ppm: 8.01 (1H, s), 6.90 (1H, t, J=8.1 Hz), 6.35 (2H, d J=8.1 Hz), 6.12 (1H, t, J=6.7 Hz), 5.18-5.17 (1H, m), 4.27-4.20 (1H, t, J=5.8 Hz), 5.19 (1H, m), 4.37 (3H, m), 2.43-2.32 (2H, m), 2.08 (3H, s), 2.05 (3H, s).

ESI-MS (m/z): 4.98.04 (M+H)$^+$

IR (cm$^{-1}$): 3390, 3301 m.p.° C.: 249.6-250.0° C.

Preparation Example 3

Preparation of the Compound (18)

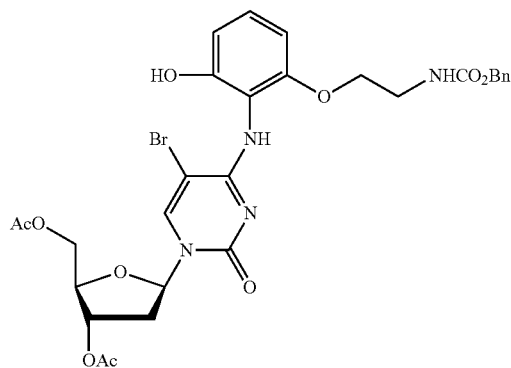

(18)

Under argon stream, the compound (17) (2.60 g, 5.21 mmol), benzyl 2-hydroxyethylcarbamate (1.33 g, 6.8 mmol), and triphenylphosphine (2.23 g, 8.5 mmol) were azeotroped with anhydrous acetonitrile (40 mL) three times and anhydrous dichloromethane (32 mL). Anhydrous dichloromethane (36 mL) was added to the residue and the mixture was stirred in an ice bath. Diisopropyl azodicarboxylate (4.47 mL, 8.5 mmol) was added dropwise to the mixture and the mixture was allowed to warm to room temperature and stirred. After 21 hours, the reaction liquid was washed with water and a saturated saline solution. The organic phase was dried over anhydrous sodium sulfate and the solvent was distilled off under reduced pressure. The residue was purified by silica gel column chromatography (60N available from Kanto Chemical Co., Inc.; ethyl acetate:chloroform=1:2 to ethyl acetate) to obtain 1.39 g of the compound (18) with a yield of 39%.

$^1$H-NMR (400 MHz, CDCl$_3$) δ ppm: 7.92 (1H, s), 7.33 (5H, m), 7.05 (1H, t, J=8.2 Hz), 6.71 (1H, d, J=8.4 Hz), 6.42 (1H, t, J=8.2 Hz), 6.24 (1H, t, J=7.1 Hz), 5.20 (1H, m), 5.10 (2H, s), 4.36 (2H, m), 4.31 (1H, m), 4.13 (2H, m), 3.66 (2H, m), 2.69 (1H, m), 2.12 (3H, s), 2.09 (4H, m).

ESI-MS (m/z): 675.68 (M+H)$^+$

IR (cm$^1$): 3339, 1741, 1671, 1230, 1093

Preparation Example 4

Preparation of the Compound (19)

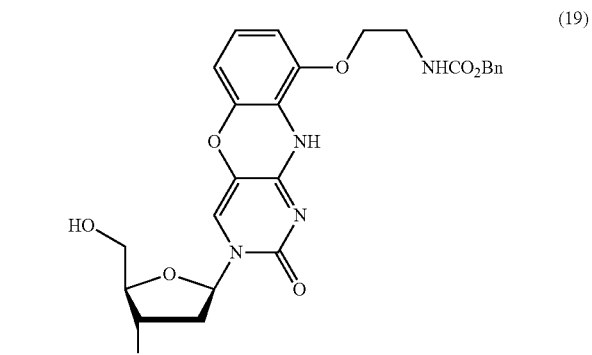

(19)

Under argon stream, 7 M ammonia-methanol (80 mL, 3.66 mmol) was added to the compound (18) (1.55 g, 2.29 mmol) and the mixture was stirred at room temperature. After 72 hours, the solvent of the reaction liquid was distilled off under reduced pressure. The residue was purified by silica gel column chromatography (60N available from Kanto Chemical Co., Inc.; chloroform:methanol=15:1 to 9:1) to obtain 650 mg of the compound (19) with a yield of 55%.

$^1$H-NMR (400 MHz, CD$_3$OD) δ ppm: 7.70 (1H, s), 7.29 (5H, m), 6.81 (1H, t, J=8.2 Hz), 6.58 (1H, t, J=7.9 Hz), 6.41 (1H, d, J=8.2 Hz), 6.41 (1H, d, J=8.2 Hz), 5.11 (2H, s), 4.37 (1H, m), 4.05 (2H, m), 3.92 (1H, m), 3.81 (1H, dd, 3.1 Hz, 12.0 Hz), 3.73 (1H, dd, J=3.7 Hz, 12.0 Hz), 3.53 (2H, m), 2.33 (1H, m), 2.12 (1H, m).

ESI-MS (m/z): 511.29 (M+H)$^+$

IR (cm$^{-1}$): 3408, 3199, 1722, 1681, 776 m.p.° C.: 131.2-132.0° C.

Preparation Example 5

Preparation of the Compound (26)

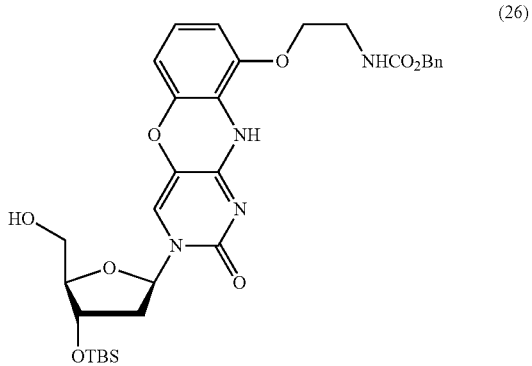

(26)

(where TBS is a tert-butyldimethylsilyl group)

To a solution of the compound (19) (655 mg, 1.28 mmol), which had been azeotroped with anhydrous pyridine, in anhydrous pyridine (11.5 mL), under argon stream, dimethoxytrityl chloride (652 mg, 1.92 mmol) was added and stirred at room temperature. After 1.5 hours, the reaction liquid was diluted with CHCl$_3$ (30 mL) and washed with a saturated sodium bicarbonate aqueous solution. The organic phase was dried over sodium sulfate, and the solvent was distilled off under reduced pressure. The resultant crude product was purified by silica gel column chromatography (60N available from Kanto Chemical Co., Inc.; chloroform to chloroform:methanol=50:1 to methanol). To a solution of the resultant brown solid in anhydrous N,N-dimethylformamide (3.7 mL), imidazole (206 mg, 3.023 mmol) and tert-butyldimethylsilane chloride (373 mg, 2.015 mmol) were added and stirred at room temperature. After 3 hours, the reaction liquid was diluted with chloroform (20 mL), washed with a saturated sodium bicarbonate aqueous solution. The organic phase was dried over sodium sulfate, and the solvent was distilled off under reduced pressure. To the resultant crude product, 3% trichloroacetic acid (30 mL) was added and stirred at room temperature. After 1 hour, the reaction liquid was diluted with a saturated sodium bicarbonate aqueous solution (15 mL) and extracted with ethyl acetate. The organic phase was dried over sodium sulfate. The solvent was distilled off under reduced pressure and the resultant residue was purified by silica gel column chromatography (60N available from Kanto Chemical Co., Inc.; chloroform/methanol=50/1) to obtain 540 mg of the compound (26) with a yield of 73%.

$^1$H-NMR (400 MHz, CDCl$_3$) δ ppm: 7.42 (1H, s), 7.27 (5H, m), 6.77 (1H, t, J=8 Hz), 6.36 (2H, m), 6.12 (1H, t, J=6 Hz), 5.08 (2H, m), 4.45 (1H, m), 3.97 (2H, m), 3.91 (2H, m), 3.73 (1H, m), 3.56 (1H, Br), 2.30 (2H, m), 0.86 (9H, s), 0.06 (3H, s), 0.05 (3H, s). ESI-MS (m/z): 625.3524 (M+H)$^+$ Preparation Example 6

Preparation of the Compound (27)

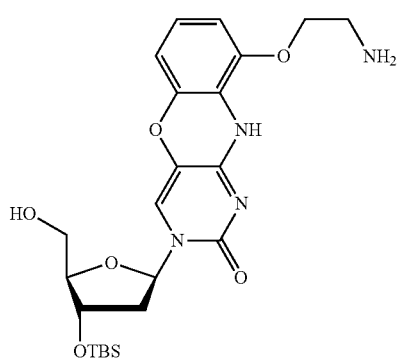

(27)

Palladium hydroxide-carbon (100 mg) and cyclohexene (1 mL) were added to a solution of the compound (26) (100 mg, 0.16 mmol) in methanol (2 mL) and the mixture was heated to reflux. After 1.5 hours, the reaction solution was filtered and the filtrate was distilled under reduced pressure. The residue was purified by silica gel column chromatography (60N available from Kanto Chemical Co., Inc.; chloroform, methanol:chloroform:triethylamine=5:95:1) to obtain 53 mg of the compound (27) as a yellow solid with a yield of 68%.

$^1$H-NMR (400 MHz, CD$_3$OD) δ ppm: 7.67 (1H, s), 6.83 (1H, t, J=8 Hz), 6.61 (1H, d, J=8 Hz), 6.43 (1H, d, J=8 Hz), 6.20 (1H, t, J=6 Hz), 4.49 (1H, m), 4.07 (2H, t, J=5 Hz), 3.90 (1H, m), 3.79 (1H, dd, J=3 Hz, 12 Hz), 3.70 (1H, dd, J=3 Hz, 12 Hz), 3.09 (2H, t, J=5 Hz), 2.28 (1H, m), 2.13 (1H, m), 0.92 (9H, s), 0.12 (6H, s).

IR ν$_{max}$ (film): 3275, 1672, 1563, 1261.

ESI-MS (m/z): 491.2 (M+H)$^+$.

Yellow Carame

Preparation Example 7

Preparation of the Compound (28)

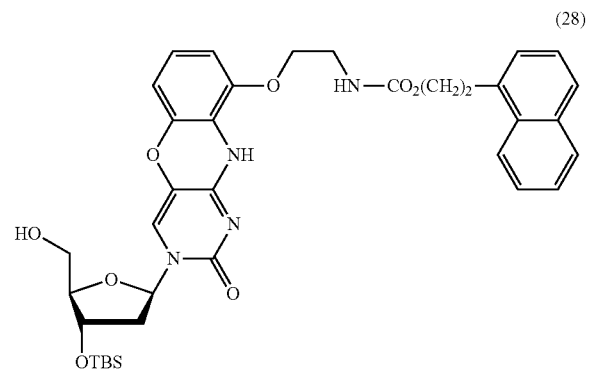

(28)

To a solution of the compound (27) (50 mg, 0.10 mmol) in anhydrous pyridine (2 mL) in an ice bath, chlorotrimethylsilane (33 μL, 0.26 mmol) was added dropwise and the mixture was stirred at room temperature. After 30 minutes, 2-(2-naphthyl)ethyl 1H-imidazole-1-carboxylate (100 mg) was added and the mixture was stirred at room temperature. After 21 hours, 28% aqueous ammonia was added to quench the reaction. Extraction was carried out using chloroform and the organic phase was dried over sodium sulfate, and the solvent was distilled off under reduced pressure. The resultant crude product was purified by silica gel chromatography (60N available from Kanto Chemical Co., Inc.; chloroform:methanol=50:1) to obtain 29 mg of the compound (28) with a yield of 43%.

$^1$H-NMR (400 MHz, CDCl$_3$) δ ppm: 8.07 (1H, d, J=8 Hz), 7.89 (1H, s), 7.79 (1H, d, J=8 Hz), 7.67 (1H, m), 7.45 (2H, m), 7.33 (2H, m), 7.15 (1H, Br), 6.89 (1H, t, J=8 Hz), 6.46 (1H, d, J=9 Hz), 6.33 (1H, d, J=8 Hz), 6.17 (1H, t, J=6 Hz), 4.50 (1H, m), 4.38 (2H, t, J=7 Hz), 3.96 (4H, m), 3.79 (1H, m), 3.61 (2H, m), 3.41 (2H, t, J=8 Hz), 2.35 (1H, m), 2.18 (1H, m), 0.88 (9H, s), 0.07 (6H, s).

IR ν$_{max}$ (film): 3275, 1709, 1473, 1087.

ESI-MS (m/z): 689.3 (M+H)$^+$.

Preparation Example 8

Preparation of the Compound (29)

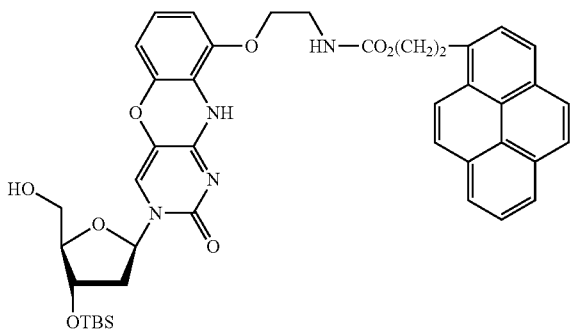

To a solution of the compound (27) (50 mg, 0.10 mmol) in anhydrous pyridine (2 mL) in an ice bath, chlorotrimethylsilane (33 μL, 0.26 mmol) was added dropwise and the mixture was stirred at room temperature. After 30 minutes, 2-(1-pyrenyl)ethyl 1H-imidazole-1-carboxylate (100 mg) was added and the mixture was stirred at room temperature. After 21 hours, 28% aqueous ammonia was added to quench the reaction. Extraction was carried out using chloroform and the organic phase was dried over sodium sulfate, and the solvent was distilled off under reduced pressure. The resultant crude product was purified by silica gel chromatography (60N available from Kanto Chemical Co., Inc.; chloroform:methanol=50:1) to obtain 18 mg of the compound (29) with a yield of 24%.

$^1$H-NMR (400 MHz, CDCl$_3$) δ ppm: 824 (1H, d, J=9 Hz), 7.96 (8H, m), 7.54 (1H, s), 6.77 (1H, Br), 6.61 (1H, m), 6.20 (1H, d, J=8 Hz), 6.13 (1H, d, J=9 Hz), 6.07 (1H, m), 4.50 (3H, m), 3.92 (2H, m), 3.79 (3H, m), 3.63 (2H, m), 3.53 (2H, m), 2.24 (1H, m), 2.17 (1H, m), 0.87 (9H, s), 0.07 (6H, s).

IR ν$_{max}$ (film): 3230, 1710, 1473, 1088.
ESI-MS (m/z): 763.4 (M+H)$^+$.

Preparation Example 9

Preparation of the Compound (30)

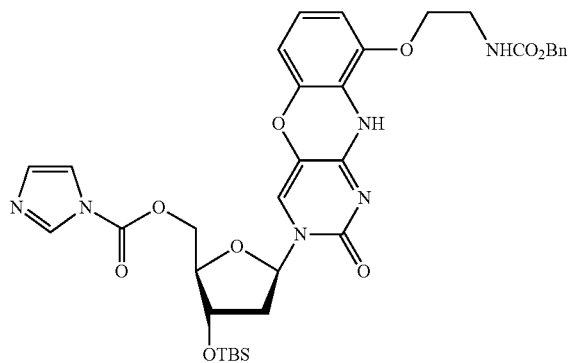

Under argon stream, to a solution of the compound (26) (35 mg, 0.06 mmol) in anhydrous dichloromethane (1 mL) at room temperature, N,N'-carbonyldiimidazole (18 mg, 0.11 mmol) was added and the mixture was stirred. After 2.5 hours, the solvent of the reaction liquid was distilled off under reduced pressure to obtain 39 mg of the compound (30) with a yield of 98%.

$^1$H-NMR (400 MHz, CDCl$_3$) δ ppm: 8.19 (1H, s), 7.44 (1H, s), 7.28 (1H, s), 7.08 (1H, s), 6.78 (1H, t, J=7.9 Hz), 6.44 (1H, d, J=7.9 Hz), 6.40 (1H, d, J=7.9 Hz), 6.14 (1H, t, J=6.1 Hz), 5.92 (1H, Br), 5.08 (2H, s), 4.67 (1H, dd, J=3.1 Hz, 12.5 Hz), 4.57 (1H, dd, J=11.6 Hz), 4.33 (1H, m), 4.11 (1H, m), 4.04 (2H, m), 3.58 (2H, m), 2.42 (1H, m), 2.23 (1H, m), 0.87 (9H, s), 0.06 (6H, s).

ESI-MS (m/z): 719.40 (M+H)$^+$.

Preparation Example 10

Preparation of the Compound (31)

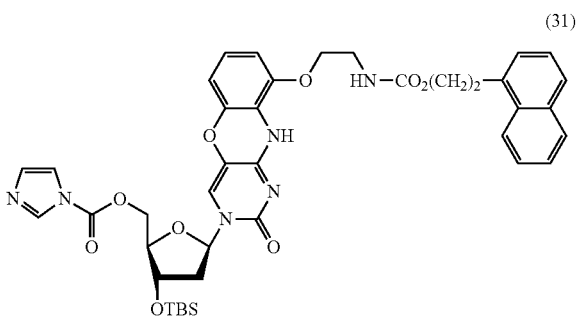

Under argon stream, to a solution of the compound (28) (29 mg, 0.04 mmol) in anhydrous dichloromethane (3 mL) at room temperature, N,N'-carbonyldiimidazole (14 mg, 0.08 mmol) was added and the mixture was stirred. After 2.5 hours, the solvent of the reaction liquid was distilled off under reduced pressure to obtain 32 mg of the compound (31) with a yield of 91%.

$^1$H-NMR (400 MHz, CDCl$_3$) δ ppm: 9.21 (1H, Br), 8.19 (1H, s), 8.00 (1H, d, J=8 Hz), 7.79 (1H, m), 7.67 (1H, m), 7.41 (7H, m), 6.78 (1H, t, J=8 Hz), 6.40 (1H, t, J=9 Hz), 6.29 (1H, m), 6.15 (1H, m), 4.66 (1H, dd, J=12 Hz), 4.57 (1H, m), 4.39 (1H, m), 4.31 (2H, m), 4.12 (1H, m), 3.97 (1H, m), 3.53 (2H, m), 3.37 (1H, m), 3.31 (2H, t, J=7 Hz), 2.42 (1H, m), 2.22 (1H, m), 0.86 (9H, s), 0.05 (6H, s).

ESI-MS (m/z): 783.40 (M+H)$^+$.

Preparation Example 11

Preparation of the Compound (32)

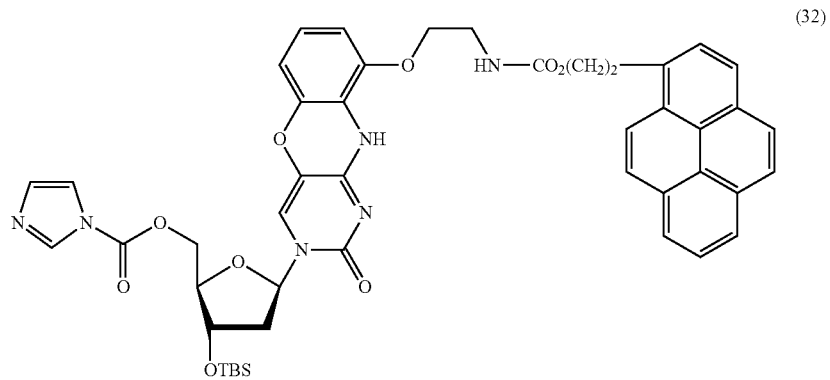

Under argon stream, to a solution of the compound (29) (25 mg, 0.03 mmol) in anhydrous dichloromethane (3 mL) at room temperature, N,N'-carbonyldiimidazole (11 mg, 0.06 mmol) was added and the mixture was stirred. After 2.5 hours, the solvent of the reaction liquid was distilled off under reduced pressure to obtain 28 mg of the compound (32) with a yield of 96%.

Example 1

Preparation of Silica Gel Particles (33)

Average Particle Diameter 10 μm

To a solution of the compound (30) (0.04 mmol) in anhydrous dichloromethane (1 mL), amino-treated silica gel NH SMB 100-10 (manufactured by Fuji Silysia Chemical Ltd; average particle diameter: 9.2 μm, pore volume: 0.57 mL/g, carbon content: 4.0 wt %) (100 mg) and imidazole (11 mg, 0.16 mmol) were added and the mixture was shaken (300 rpm) at room temperature. After 3 days, the silica gel particles were separated by filtration and washed thoroughly with chloroform and methanol to obtain the silica gel particles (33) in the heading.

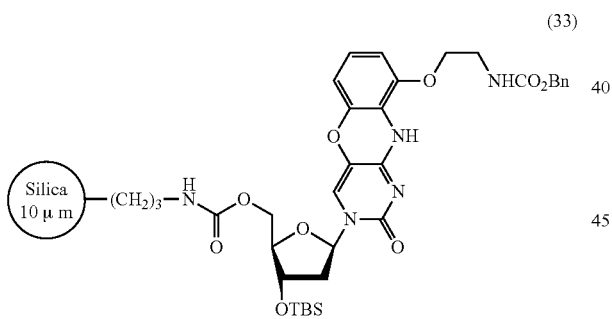

Example 2

Preparation of Silica Gel Particles (34)

Average Particle Diameter 10 μm

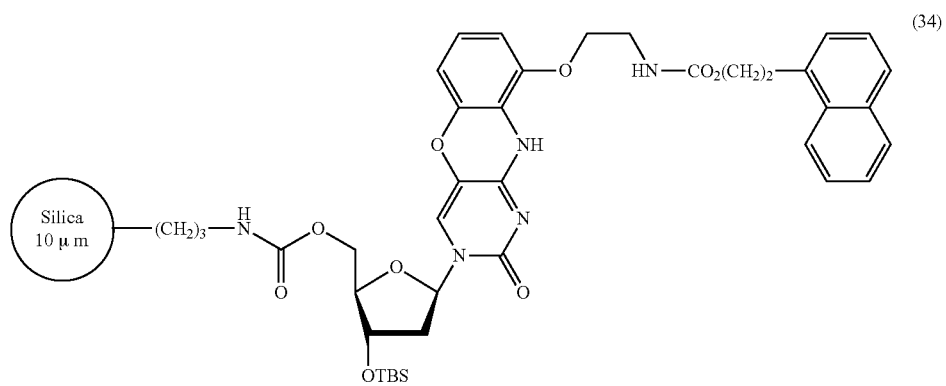

To a solution of the compound (31) (0.04 mmol) in anhydrous dichloromethane (1 mL), amino-treated silica gel NH SMB 100-10 (manufactured by Fuji Silysia Chemical Ltd; average particle diameter: 9.2 μl, pore volume: 0.57 carbon content: 4.0 wt %) (100 mg) and imidazole (11 mg, 0.16 mmol) were added and the mixture was shaken (300 rpm) at room temperature. After 3 days, the silica gel particles were separated by filtration and the washed thoroughly with chloroform and methanol to obtain the silica gel particles (34) in the heading.

Example 3

Preparation of Silica Gel Particles (35)

Average Particle Diameter 10 μm

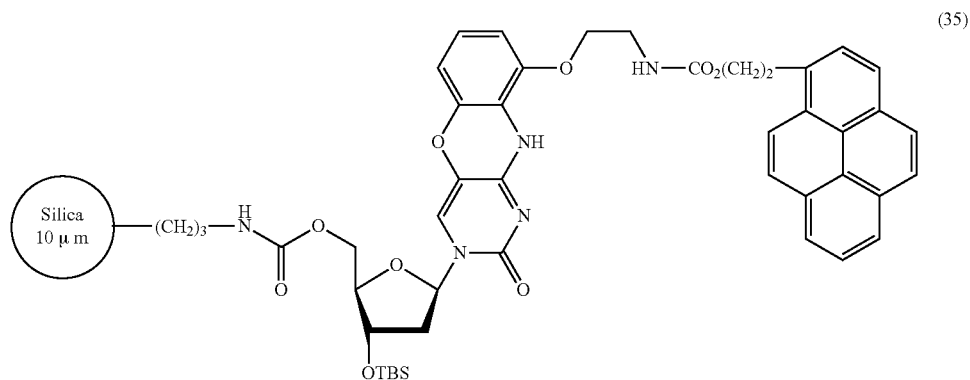

To a solution of the compound (32) (0.04 mmol) in anhydrous dichloromethane (1 mL), amino-treated silica gel NH SMB 100-10 (manufactured by Fuji Silysia Chemical Ltd; average particle diameter: 9.2 μm, pore volume: 0.57 mL/g, carbon content: 4.0 wt %) (100 mg) and imidazole (11 mg, 0.16 mmol) were added and the mixture was shaken (300 rpm) at room temperature. After 3 days, the silica gel particles were separated by filtration and washed thoroughly with chloroform and methanol to obtain the silica gel particles (35) in the heading.

Preparation Example 12

Preparation of the Compound (36)

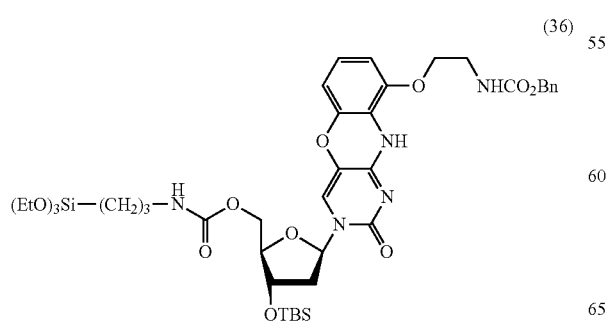

To a solution of the compound (30) (28 mg, 0.04 mmol) in anhydrous THF (2 mL), 3-aminopropyltriethoxysilane (50 μL, 0.24 mmol) was added and the mixture was stirred at room temperature. After 18 hours, the solvent was distilled off under reduced pressure. The residue was purified by silica gel chromatography (FL-60D; dichloromethane) to obtain 15 mg of the compound (36) with a yield of 43%.

$^1$H-NMR (400 MHz, CDCl$_3$) δ ppm: 7.29 (6H, m), 6.76 (1H, t, 0.1=7.9, 8.2 Hz), 6.44 (1H, d, J=7.9 Hz), 6.39 (1H, d, J=8.5 Hz), 6.19 (1H, m), 5.79 (1H, Br), 5.19 (1H, Br), 5.10 (2H, s), 4.25 (3H, m), 3.78 (6H, q, J=7.0 Hz), 3.58 (2H, m), 3.20 (2H, m), 2.39 (1H, m), 2.12 (1H, m), 1.19 (9H, t, J=7.0 Hz), 0.95 (2H, m), 0.86 (9H, s), 0.62 (2H, m), 0.04 (6H, s).

ESI-MS (m/z): 827.7957 (M+H)$^+$

IR (cm$^1$): 3326, 2930, 1698, 1474, 1102

Preparation Example 13

Preparation of the Compound (37)

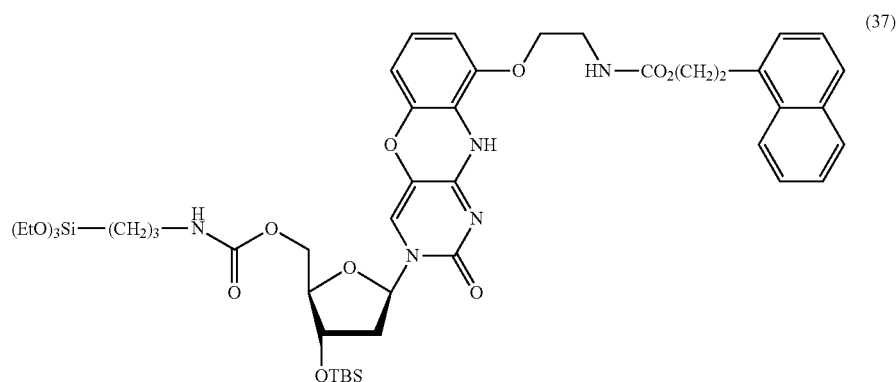

To a solution of the compound (31) (30 mg, 0.04 mmol) in anhydrous THF (1 mL), 3-aminopropyltriethoxysilane (30 μL, 0.14 mmol) was added and the mixture was stirred at room temperature. After 18 hours, the solvent was distilled of under reduced pressure. The residue was purified by silica gel chromatography (FL-60D; dichloromethane) to obtain 14 mg of the compound (37) with a yield of 38%.

$^1$H-NMR (400 MHz, CDCl$_3$) δ ppm: 9.28 (1H, s), 8.00 (1H, d, J=8 Hz), 7.80 (1H, m), 7.69 (1H, m), 7.39 (5H, m), 6.78 (1H, m), 6.40 (2H, m), 6.16 (1H, m), 4.45 (1H, m), 4.26 (4H, m), 4.01 (2H, m), 3.79 (6H, m), 3.58 (1H, m), 3.43 (2H, m), 3.34 (2H, m), 3.21 (2H, m), 2.41 (1H, m), 1.97 (1H, m), 1.63 (2H, m), 1.18 (9H, m), 0.87 (9H, s), 0.62 (2H, s), 0.06 (3H, s).

IR ν$_{max}$ (film): 3320, 1704, 1473, 1102.

ESI-MS (m/z): 937.34 (M+H)$^+$.

Preparation Example 14

Preparation of the Compound (38)

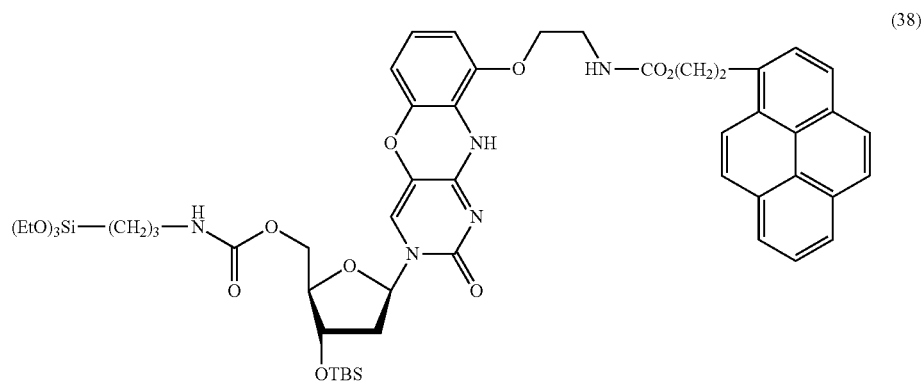

To a solution of the compound (32) (40 mg, 0.05 mmol) in anhydrous THF (1.5 mL), 3-aminopropyltriethoxysilane (40 µL, 0.19 mmol) was added and the mixture was stirred at room temperature. After 24 hours, the solvent was distilled off under reduced pressure. The residue was purified by silica gel chromatography (FL-60D; dichloromethane) to obtain 18 mg of the compound (38) with a yield of 36%.

$^1$H-NMR (400 MHz, CDCl$_3$) δ ppm: 8.10 (9H, m), 7.50 (1H, s), 6.73 (1H, m), 6.32 (2H, m), 6.14 (1H, t, J=5.8 Hz), 4.43 (1H, m), 4.30 (2H, m), 4.25 (2H, m), 4.03 (1H, m), 4.30 (2H, m), 4.25 (2H, m), 4.03 (1H, m), 3.92 (2H, m), 3.78 (6H, m), 3.57 (2H, m), 3.49 (2H, m), 3.21 (2H, m), 2.34 (1H, m), 2.00 (1H, m), 1.64 (2H, m), 1.21 (9H, m), 0.87 (9H, s), 0.61 (2H, s), 0.05 (6H, s).

IR ν$_{max}$ (film): 3132, 1704, 1473, 1063.
ESI-MS (m/z): 1011.53 (M+H)$^+$.

Example 4

Preparation of Silica Gel Particles (39)

Average Particle Diameter 100 nm

The compound (36) (0.01 mmol) was added to a suspension of 100 mg of Microsilica (Hydro 2000G, average particle diameter: 0.1 µm, manufactured by Elkem Material) in purified water (5 mL), ethanol (5 mL), and acetic acid (5 mL) and the mixture was refluxed at 80° C. After 36 hours, ethanol was distilled off under reduced pressure. The acetic acid solution was neutralized with a saturated sodium bicarbonate solution. The silica gel particles were separated by filtration and washed thoroughly with purified water and acetone to obtain the silica gel particles (39) in the heading.

Example 5

Preparation of Silica Gel Particles (40)

Average Particle Diameter 100 nm

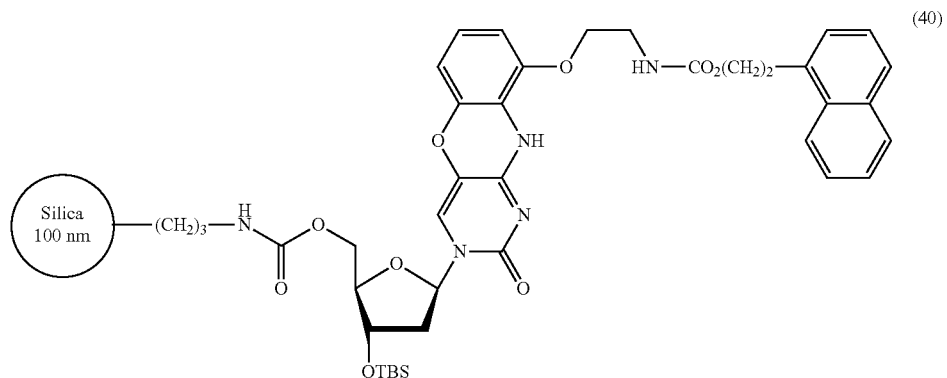

The compound (37) (0.01 mmol) was added to a suspension of 100 mg of Microsilica (Hydro 20006, average particle diameter: 0.1 μm, manufactured by Elkem Material) in purified water (5 mL), ethanol (5 mL), and acetic acid (5 mL) and the mixture was refluxed at 80° C. After 36 hours, ethanol was distilled off under reduced pressure. The acetic acid solution was neutralized with a saturated sodium bicarbonate solution. The silica gel particles were separated by filtration and washed thoroughly with purified water and acetone to obtain the silica gel particles (40) in the heading.

Example 6

Preparation of Silica Gel Particles (41)

Average Particle Diameter 100 nm

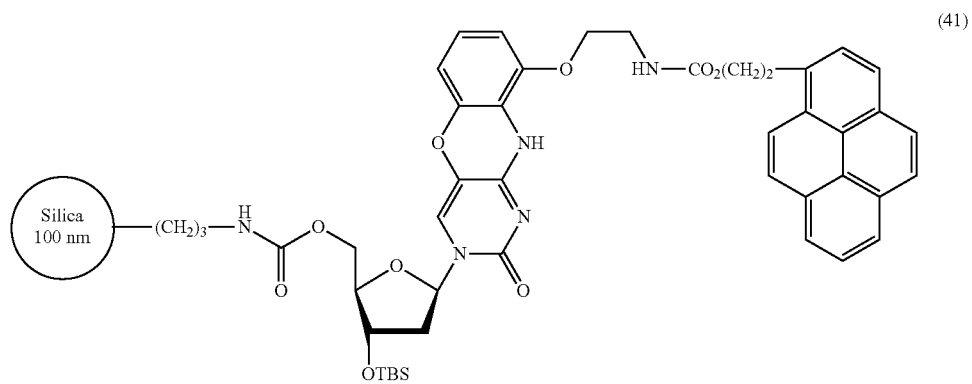

The compound (38) (0.01 mmol) was added to a suspension of 100 mg of Microsilica (Hydro 2000G, average particle diameter: 0.1 μm, manufactured by Elkem Material) in purified water (5 mL), ethanol (5 mL), and acetic acid (5 mL) and the mixture was refluxed at 80° C. After 36 hours, ethanol was distilled off under reduced pressure. The acetic acid solution was neutralized with a saturated sodium bicarbonate solution. The silica gel particles were separated by filtration and washed thoroughly with purified water and acetone to obtain the silica gel particles (41) in the heading.

Test Example 1

Elemental Analysis

The silica gel particles (33) to (35) and (39) to (41) were subjected to elemental analysis to obtain nitrogen contents %, which were used to calculate the content of the probe molecule contained in each kind of particles. The results are shown in Table 1.

TABLE 1

| Silica gel particles | Nitrogen contents (%) | Probe molecule contents (μmol/100 mg) |
| --- | --- | --- |
| Silica (NH SMB 100-10) | 1.33 | 0 |
| Silica gel particles (33) | 1.83 | 8.91 |
| Silica gel particles (34) | 1.78 | 8.05 |
| Silica gel particles (35) | 2.26 | 16.61 |
| Silica (Hydro 2000G) | 0 | 0 |
| Silica gel particles (39) | 0.2 | 2.85 |
| Silica gel particles (40) | 0.4 | 5.72 |
| Silica gel particles (41) | 0.2 | 2.09 |

As is clear from Table 1, it was found that the silica gel particles (35) to (37) and (39) to (41) all contained the probe molecule.

Test Example 2

Observation Under a Fluorescence Microscope

2 μL of a 25 μM 8-oxo-dG aqueous solution was added to the silica gel particles (33) to (35) and allowed to stand at room temperature for water evaporation to obtain samples. 2 μL of a 25 μM dG aqueous solution was added to the silica gel particles (33) to (35) and allowed to stand at room temperature for water evaporation to obtain samples. The samples were observed under a fluorescence microscope to determine the change of fluorescence reactivity.

An excitation wavelength of 345 nm and a fluorescence wavelength of 455 nm were used for the measurement.

Figure 3:
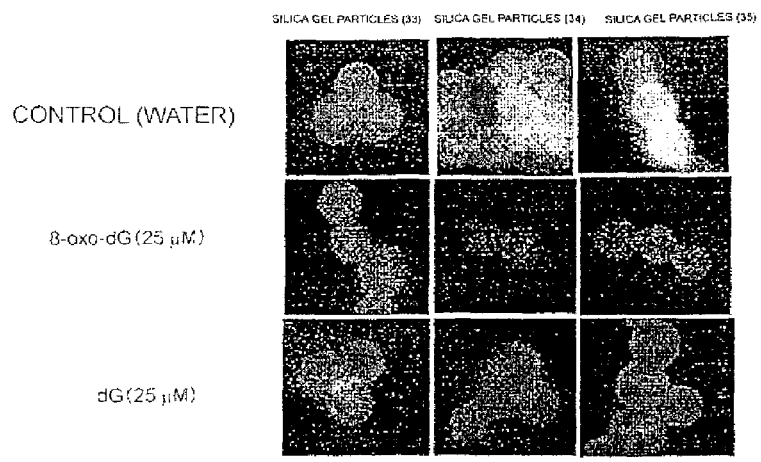
FIG. 3 is fluorescence microscopy photographs showing fluorescence reactivity of the silica gel particles (33) to (35).

The photographs obtained as a result of observation are shown in FIG. 3.

As is clear from the photographs, obvious fluorescence quenching was observed in all the samples to which the 8-oxo-dG aqueous solution has been added as compared to the control (water), whereas such fluorescence quenching was not observed in the samples to which the aqueous dG solutions has been added.

Test Example 3

Evaluation of the Ability to Recognize 8-Oxo-dG

For the silica gel particles (33) to (35) prepared as described above, the ability to recognize 8-oxo-dG was evaluated as follows.

Polystyrene blackplates were used as measuring plates. A near-ultraviolet episcopic illuminator (365 nm) and a Y515 filter (Y515-Di) were used for evaluation. A 10 mM solution of nucleic acid base (8-oxoG, G) in purified water was prepared and diluted to prepare a 5 mM stock solution. The solution was added in units of μL to each kind of silica gel particles. After air drying, the fluorescence intensities of the silica gel particles were measured by using a cold CCD camera system LAS 4000 manufactured by Fujifilm Corporation. Detection method: fluorescence DAPI, light source: UV (365 nm EPI), filter: Y515-Di, sensitivity: standard, exposure type: precision, exposure time: AUTO, tray position: No. 1

Figure 4:
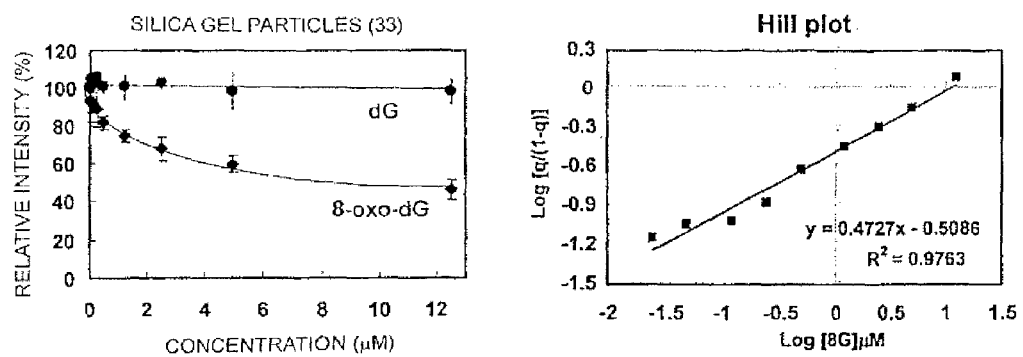
FIG. 4 shows a graph of the concentrations of 8-oxo-dG and dG versus the relative fluorescence intensities of the silica gel particles (33) (left) and a graph obtained by converting the relationship of the concentration of 8-oxo-dG versus the quenching ratio to a hill plot (right).

A graph of the concentrations of 8-oxo-dG and dG versus the relative fluorescence intensities of the silica gel particles (33) is shown on the left in FIG. 4; and a graph obtained by converting the relationship of the concentration of 8-oxo-dG versus the quenching ratio to a hill plot is shown on the right in FIG. 4. A graph of the concentrations of 8-oxo-dG and dG versus the relative fluorescence intensities of the silica gel particles (34) is shown on the left in FIG. 5; and a graph obtained by converting the relationship of the concentration of 8-oxo-dG versus the quenching ratio to a hill plot is shown on the right in FIG. 5. A graph of the concentrations of 8-oxo-dG and dG versus the relative fluorescence intensities of the silica gel particles (35) is shown on the left in FIG. 6; and a graph obtained by converting the relationship of the concentration of 8-oxo-dG versus the quenching ratio to a hill plot is shown on the right in FIG. 6.

Figure 10:
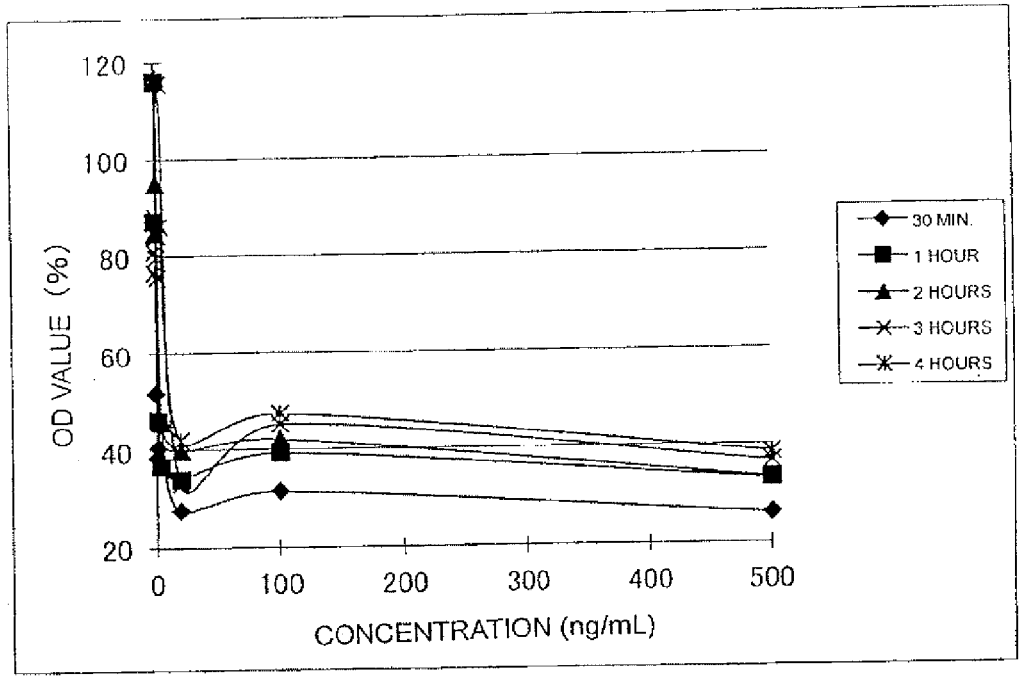
FIG. 10 is a graph illustrating the attenuation rates (relative intensity % as compared to that before addition) of the optical density values (OD values) of the silica gel particles (39) in an 8-oxo-dG concentration range of 0 ng/mL to 500 ng/mL measured 30 minutes to 4 hours after addition of 8-oxo-dG standard solutions (concentrations: 0 ng/mL to 500 ng/mL) to a microplate in which the silica gel particles (39) had been dried to adhere to the surfaces of the wells.
Figure 11:
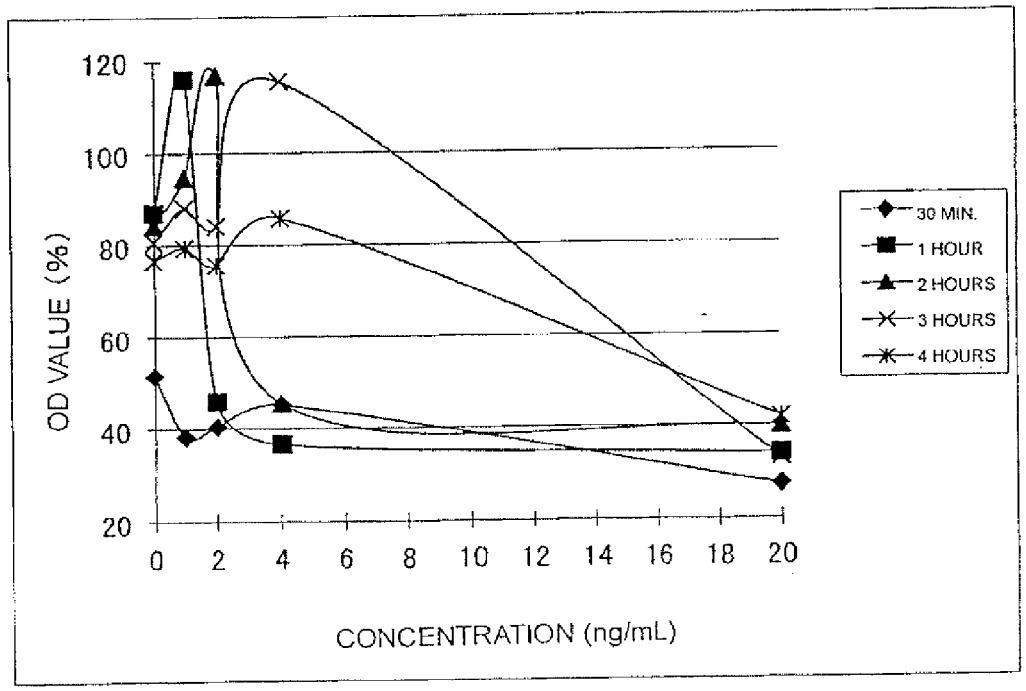
FIG. 11 is a graph illustrating the attenuation rates (relative intensity % as compared to that before addition) of the optical density values (OD values) of the silica gel particles (39) in an 8-oxo-dG concentration range of 0 ng/mL to 20 ng/mL measured 30 minutes to 4 hours after addition of 8-oxo-dG standard solutions (concentrations: 0 ng/mL to 500 ng/mL) to a microplate in which the silica gel particles (39) had been dried to adhere to the surfaces of the wells.

From the left figures of FIGS. 10 to 12, it was found that the fluorescence intensities of the silica gel particles (33) to (35) decreased as the concentration of 8-oxo-dG increased whereas the concentration of dG had substantially no influence on the fluorescence intensities.

Figure 5:
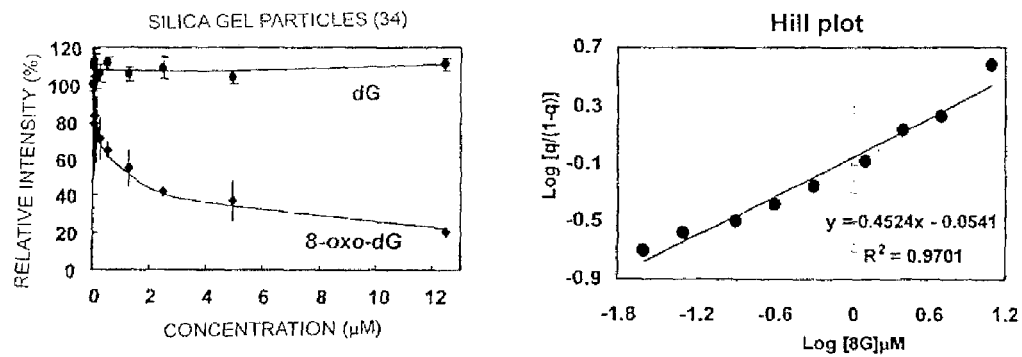
FIG. 5 shows a graph of the concentrations of 8-oxo-dG and dG versus the relative fluorescence intensities of the silica gel particles (34) (left) and a graph obtained by converting the relationship of the concentration of 8-oxo-dG versus the quenching ratio to a hill plot (right).
Figure 6:
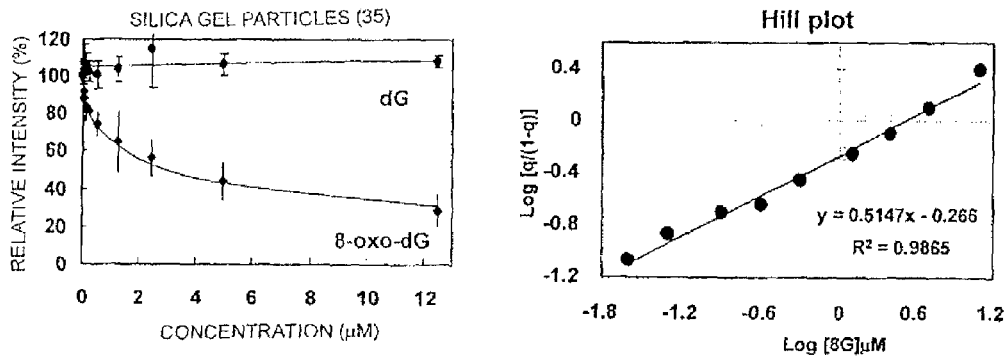
FIG. 6 shows a graph of the concentrations of 8-oxo-dG and dG versus the relative fluorescence intensities of the silica gel particles (35) (left) and a graph obtained by converting the relationship of the concentration of 8-oxo-dG versus the quenching ratio to a hill plot (right).

The right figures of FIGS. 4 to 6, which are hill plots of the concentrations of 8-oxo-dG versus the fluorescence quenching ratios of the silica gel particles (33) to (35), show good linearity, demonstrating that the particles cause fluorescence quenching in a manner dependent on the concentration of 8-oxo-dG.

From the foregoing, it was found that quantitative assay is possible if 8-oxo-dG is present in a concentration of 25 nM or more, which is the lowest concentration in the graphs and that the silica gel particles (33) to (35) may be used for quantitative assay of urine, which is reported to contain 8-oxo-dG approximately in a concentration of 10 ng/mL to 20 ng/mL (35 nM to 70 nM).

Test Example 4

Competitive Test of 8-Oxo-dG and dG

To the silica gel particles (33) to (35) prepared as described above, 2.5 pmol of 8-oxo-dG and various concentrations of dG (0, 2.5, 5, 12, 5, 25, 50, 125, 250 pmol) were added and the fluorescence intensities were measured to evaluate the influence of dG on the fluorescence quenching by 8-oxo-dG.

Figure 7:
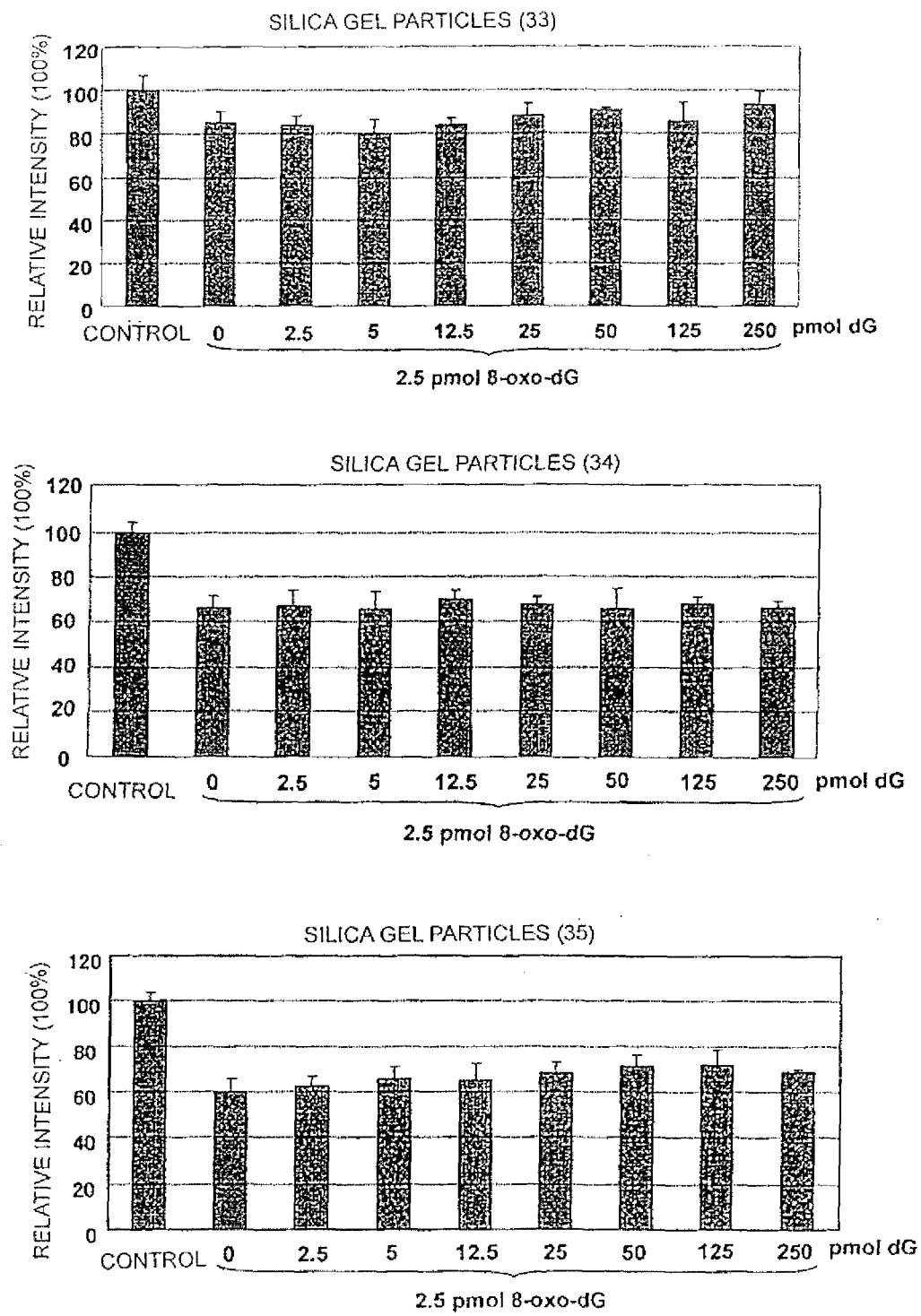
FIG. 7 is a graph illustrating the effect of the concentrations of dG (0 to 100 times the concentration of 8-oxo-dG) on the fluorescence quenching of the silica gel particles (33) to (35) with 8-oxo-dG.

The results are shown in FIG. 7.

As is clear from FIG. 7, it was found that the fluorescence quenching of the silica gel particles (33) to (35) by 8-oxo-dG is hardly influenced by dG.

From the foregoing, it is clear that quantitative assay of 8-oxo-dG with high sensitivity is possible in an aqueous sample solution containing both 8-oxo-dG and dG with little influence of the concentration of dG.

Test Example 5

Determination of the Concentration-Dependent Brightness Attenuation Rate by Using a Multiplate Reader 1) Experimental Procedure 4 μL of an aqueous suspension of 40 ng of the silica gel particles (33) with an average particle diameter of 10 μm was placed in each well of a 384-well microplate (manufactured by Corning Inc.).

The plate was allowed to stand in a dry heat oven at 50° C. (EYELA NDO-601SD) for 2 hours for water evaporation to allow the silica gel particles to adhere to the well surface.

2 μL of each of aqueous sample solutions (aqueous solutions of 8-oxo-dG standard (Wako Pure Chemical Industries, Ltd.)) (8-oxo-dG concentration: 0 ng/mL, 1 ng/mL, 2 ng/mL, 4 ng/mL, 20 ng/mL, 100 ng/mL, and 500 ng/mL, 4 wells for each concentration) was added and the plate was allowed to stand in a dry heat oven at 50° C.

By using the average value (N=4) of the ODs before the addition of the sample solution as a reference, the brightness attenuation rate for each time was calculated from the average value (N=4) of the optical densities (OD) measured 30 minutes, 1 hour, 2 hours, 3 hours, and 4 hours after the addition.

2) Measurement Conditions

Figure 8:
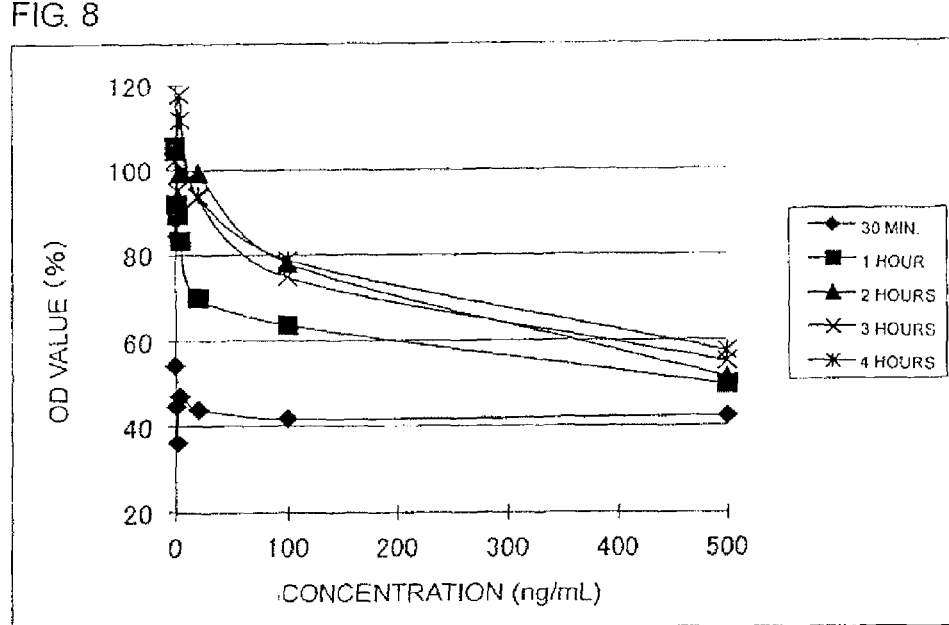
FIG. 8 is a graph illustrating the attenuation rates (relative intensity % as compared to that before addition) of the optical density values (OD values) of the silica gel particles (33) in an 8-oxo-dG concentration range of 0 ng/mL to 500 ng/mL measured 30 minutes to 4 hours after addition of 8-oxo-dG standard solutions (concentrations: 0 ng/mL to 500 ng/mL) to a microplate in which the silica gel particles (33) had been dried to adhere to the surfaces of the wells.
Figure 9:
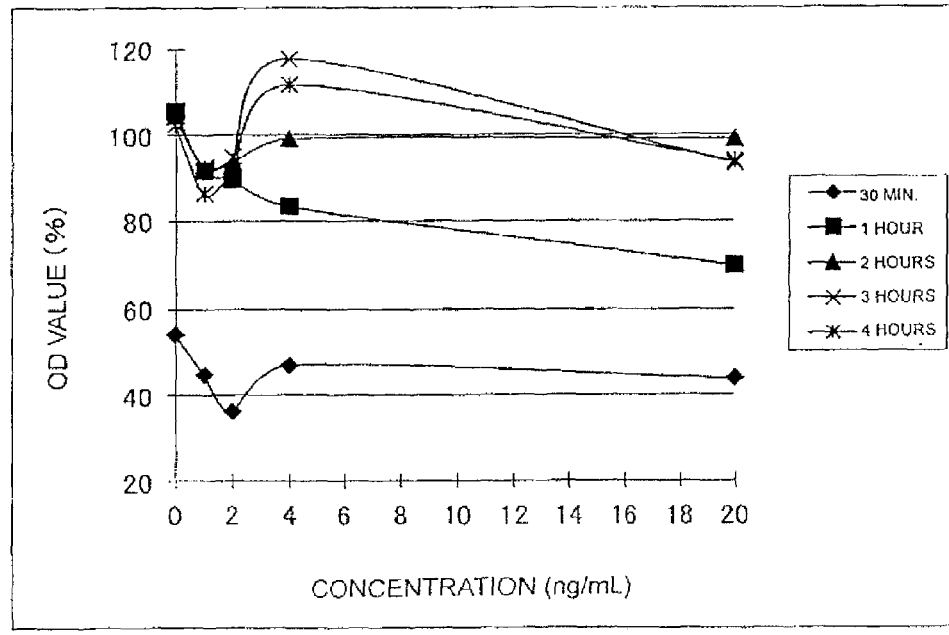
FIG. 9 is a graph illustrating the attenuation rates (relative intensity % as compared to that before addition) of the optical density values (OD values) of the silica gel particles (33) in an 8-oxo-dG concentration range of 0 ng/mL to 20 ng/mL measured 30 minutes to 4 hours after addition of 8-oxo-dG standard solutions (concentrations: 0 ng/mL to 500 ng/mL) to a microplate in which the silica gel particles (33) had been dried to adhere to the surfaces of the wells.

Instrument: Microplate reader MTP-880 Lab (manufactured by Corona Electric Co., Ltd.)
Excitement wavelength: 365 nm
Measurement wavelength: 450 nm
Number of flashes: 100
Measurement sensitivity: ×1
Mixing: 5 seconds, linear FIG. 8 shows a graph of the results of measurements at each time in an 8-oxo-dG concentration range of 0 ng/mL to 500 ng/mL, and FIG. 9 shows a graph of the results of measurements at each time in an 8-oxo-dG concentration range of 0 ng/mL to 20 ng/mL.

The above procedure was conducted except that 4 µL of an aqueous suspension of 160 ng of the silica gel particles (39) with an average particle diameter of 100 nm was used instead of 4 µL of the aqueous suspension of 40 ng of the silica gel particles (33) with an average particle diameter of 10 µm. FIG. 10 shows a graph of the results of measurements at each time in an 8-oxo-dG concentration range of 0 ng/mL to 500 ng/mL, and FIG. 11 shows a graph of the results of measurements at each time in an 8-oxo-dG concentration range of 0 ng/mL to 20 ng/mL 3) Results When the silica gel particles (33) with an average particle diameter of 10 µm was used, it was found that the concentrations correlated with the brightness attenuation rate (as the concentration of 8-oxo-dG increased, the OD value decreased) 1 hour after the addition of the sample solution in the 8-oxo-dG concentration range of 0 ng/mL to 500 ng/mL as well as in the 8-oxo-dG concentration range of 0 ng/mL to 20 ng/mL (see FIGS. 8 and 9).

As shown above, it was found that measuring the OD values 1 hour after the addition of the sample solution allows accurate and quantitative detection of 8-oxo-dG even in a sample solution containing 8-oxo-dG in a very low concentration of 0 ng/mL to 20 ng/mL When the silica gel particles (39) with an average particle diameter of 100 nm was used, it was found that the concentrations correlated with the brightness attenuation rate (as the concentration of 8-oxo-dG increased, the OD value decreased) 30 minutes to 4 hours after the addition of the sample solution) in the 8-oxo-dG concentration range of 100 ng/mL to 500 ng/mL. However, data was not obtained that shows the concentrations did not correlate with the brightness attenuation rate in the 8-oxo-dG concentration range of 20 ng/mL to 500 ng/mL (see FIGS. 10 and 11).

From FIG. 11, which shows the change in the OD values in the 8-oxo-dG concentration range of 0 ng/mL to 20 ng/mL, a phenomenon was observed that the sample emitted light (the OD value exceeded 100%) in a low concentration range of 1 ng/mL to 4 ng/mL at different times. Specifically, the sample with 1 ng/mL emitted light 1 hour after, the sample with 2 ng/mL emitted light 2 hours after, and the sample with 4 ng/mL emitted light 3 hours after the addition.

Therefore, it is suggested that even with a sample solution with a very low concentration of 1 ng/mL to 4 ng/mL, 8-oxo-dG can be quantitatively detected with high sensitivity if the time at which the sample emits light is measured.

4) Conclusion

The decrease in the brightness of the silica gel particles supporting the 8-oxo-dG-recognizing molecule changed in a rational manner, depending on the concentration of the standard 8-oxo-dG and the drying time. It is also suggested that the silica gel particles with an average particle diameter of 100 nm may be more suitable for measurement with high sensitivity than the silica gel particles with an average particle diameter of 10 µm.

Test Example 6

Practicality as an HPLC Separation Column

Study of Ability to Retain 8-oxo-dG

1) Experimental Procedure 10 mg of the silica gel particles (33) with an average particle diameter of 10 µm was packed in an HPLC precolumn, and separation and identification of 8-oxo-dG were carried out by HPLC.

2) Measurement Conditions

Instrument: HTEC-500 (Eicom Corporation) (8-oxo-dG was electrochemically detected)
ODS column: CA-SODS, 2.1 φ×150 mm
Precolumn: 100 mg of ODS particles (5 µm) for separation and 10 mg of the silica gel particles (33)
Mobile phase: phosphate buffer (pH 6.5-6.8), 2% methanol, 90 mg/L SDS
Reagent: 8-oxo-dG (Wako Pure Chemical Industries, Ltd.), 10 µL of a 500 ng/mL solution injected 3) Results It was found that the retention time of 8-oxo-dG was 28.09 minutes when the precolumn did not contain the silica gel particles (33) and 29.00 minutes when the precolumn contained the silica gel particles (33), producing a delay of 3.2% (a delay rate of 3.2%).

The peak value of 8-oxo-dG was 43.96 mV when the precolumn did not contain the silica gel particles (33) and 44.22 mV when the precolumn contained the silica gel particles (33), indicating that the peak did not decrease.

4) Conclusions

When the silica gel particles (33) that chemically support the 8-oxo-dG-recognizing molecule were placed in the flow path of the HPLC, the peak appearance of 8-oxo-dG delayed, but the peak value did not decrease. Although the mobile phase is generally phosphate buffer containing methanol as the one used in this example when HPLC and ECD (electrochemical detection) are used for detection of 8-oxo-dG, the silica gel particles (33) show a certain level of affinity for 8-oxo-dG in the phosphate buffer, showing the usefulness of the silica gel particles as a packing material for a separation column.

DESCRIPTION OF THE REFERENCE NUMERALS

1: Surfaces of fine particles
2: Fluorescent probe molecule showing a fluorescence response specific to 8-oxo-dG
3: Spacer unit
4: 8-oxo-dG
5: dG
6: Minute hydrophobic space
7: Aqueous phase
11: Aqueous sample solution
16: Fine particles having a fluorescent probe molecule showing a fluorescence response specific to 8-oxo-dG immobilized thereon
17: Column

The invention claimed is:

1. A method for quantitatively detecting 8-oxo 2'-deoxyguanosine in an aqueous sample solution, comprising the steps of:
   1) immobilizing a fluorescent probe molecule showing a fluorescence response specific to 8-oxo 2'-deoxyguanosine on surfaces of fine particles via a spacer unit and bringing the sample solution into contact with the fine particles; and
   2) measuring a physical property of the fine particles before and after the contact with the sample solution to determine a change in the physical property;
   wherein:
   the fluorescent probe molecule showing a fluorescence response specific to 8-oxo 2'-deoxyguanosine is a molecule of Formula (1):

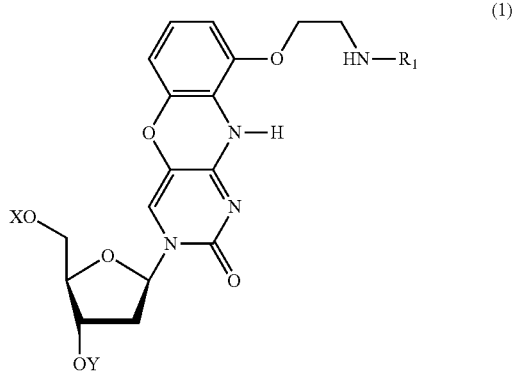

(1)

where:
   $R_1$ is a 6-amino-2-pyridyl group or —$CO_2(CH_2)_l R_2$ in which $R_2$ is a hydrogen atom or a $C_{6-16}$ aryl group, and l is an integer of 1 to 3; and
   one of X and Y is —$SiR_3R_4R_5$ in which $R_3$, $R_4$, and $R_5$ are each independently a methyl group, a tert-butyl group, or a phenyl group, and the other is —$(CH_2)_m$—NHCO— in which m is an integer of 2 to 10; and
   the fine particles are silica gel particles.

2. The method according to claim 1, wherein X is —$(CH_2)_m$—NHCO— and Y is —$SiR_3R_4R_5$.

3. The method according to claim 1, wherein the quantitative detection is carried out by drying the fine particles in a microplate well to adhere to the well, adding the aqueous sample solution to the well, and measuring fluorescence intensity of the fine particles with heating.

4. The method according to claim 1, wherein the quantitative detection is carried out by packing a column with the fine particles, passing the aqueous sample solution through the column, and measuring fluorescence intensity of the fine particles thus packed.

5. A silica gel particle having a molecule of Formula (1) immobilized on a surface of the silica gel particle via a spacer unit:

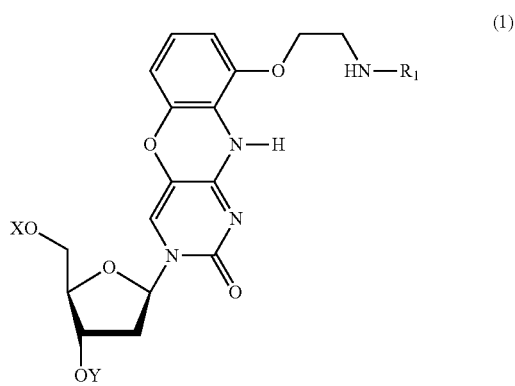

(1)

where:
   $R_1$ is a 6-amino-2-pyridyl group or —$CO_2(CH_2)_l R_2$ in which $R_2$ is a hydrogen atom or a $C_{6-16}$ aryl group, and l is an integer of 1 to 3; and one of X and Y is —$SiR_3R_4R_5$ in which $R_3$, $R_4$, and $R_5$ are each independently a methyl group, a tert-butyl group, or a phenyl group, and the other is —$(CH_2)_m$—NHCO— in which m is an integer of 2 to 10.

6. The silica gel particle according to claim 5, wherein X is —$(CH_2)_m$—NHCO—, and Y is —$SiR_3R_4R_5$.

7. A separation column for separating 8-oxo 2'-deoxyguanosine, comprising the silica gel particle as claimed in claim 5 as a packing material.

* * * * *